US012049615B2

(12) United States Patent
Li et al.

(10) Patent No.: US 12,049,615 B2
(45) Date of Patent: Jul. 30, 2024

(54) SYSTEMS AND METHODS FOR ELECTRONICALLY AND OPTICALLY MONITORING BIOLOGICAL SAMPLES

(71) Applicant: Agilent Technologies, Inc., Santa Clara, CA (US)

(72) Inventors: Nan Li, San Diego, CA (US); Xin Yao, Hangzhou (CN); Longbin Fang, Hangzhou (CN); Lingbo Kong, San Diego, CA (US); Qiting Ye, Hangzhou (CN); Caixia Yang, Hangzhou (CN); Brandon Lamarche, San Diego, CA (US); Xiaobo Wang, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 18/194,277

(22) Filed: Mar. 31, 2023

(65) Prior Publication Data

US 2023/0235266 A1    Jul. 27, 2023

Related U.S. Application Data

(62) Division of application No. 16/833,651, filed on Mar. 29, 2020.

(51) Int. Cl.
*C12M 1/00* (2006.01)
*C12M 1/32* (2006.01)
(Continued)

(52) U.S. Cl.
CPC ............ *C12M 41/06* (2013.01); *C12M 23/12* (2013.01); *C12M 31/02* (2013.01); *C12M 41/36* (2013.01);
(Continued)

(58) Field of Classification Search
CPC ...... C12M 41/06; C12M 23/12; C12M 31/02; C12M 41/36; C12M 41/48; G01N 21/6428; G01N 33/5005; G01N 2021/6439
See application file for complete search history.

(56) References Cited

U.S. PATENT DOCUMENTS 2,656,508 A    10/1953 Coulter
3,259,842 A    7/1966 Coulter et al.
(Continued)

FOREIGN PATENT DOCUMENTS

CN    106047678 B    4/2018
EP    1138758 A1    10/2001
(Continued)

OTHER PUBLICATIONS

Mohr et al. "Performance of a Thin Film Microelectrode Array for Monitoring Electrogenic Cells in Vitro." Sensors and Actuators, B34:265-269 (1996).
(Continued)

*Primary Examiner* — Samuel P Siefke
*Assistant Examiner* — Henry H Nguyen
(74) *Attorney, Agent, or Firm* — K&L Gates LLP

(57) ABSTRACT

A system for electronically and optically monitoring biological samples, the system including: a multi-well plate having a plurality of wells configured to receive a plurality of biological samples, each of the wells having a set of electrodes and a transparent window on a bottom surface of the well that is free of electrodes; an illumination module configured to illuminate the wells; a cradle configured to receive the multi-well plate, the cradle having an opening on the bottom that exposes the transparent windows of the
(Continued)

wells; and an optical imaging module movable across different wells of a same multi-well plate to capture images through the windows.

47 Claims, 26 Drawing Sheets

(51) Int. Cl.
    *C12M 1/34*           (2006.01)
    *C12M 1/36*           (2006.01)
    *G01N 21/64*         (2006.01)
    *G01N 33/50*         (2006.01)

(52) U.S. Cl.
    CPC ......... *C12M 41/48* (2013.01); *G01N 21/6428* (2013.01); *G01N 33/5005* (2013.01); *G01N 2021/6439* (2013.01)

(56) References Cited

U.S. PATENT DOCUMENTS

| | | |
|---|---|---|
| 3,742,581 A | 7/1973 | Roodvoeis |
| 3,890,201 A | 6/1975 | Cady |
| 4,072,578 A | 2/1978 | Cady et al. |
| 4,225,410 A | 9/1980 | Pace |
| 4,559,310 A | 12/1985 | Cantor et al. |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin, Jr. |
| 5,514,555 A | 5/1996 | Springer et al. |
| 5,563,067 A | 10/1996 | Sugihara et al. |
| 5,601,997 A | 2/1997 | Tchao |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guiseppi-Elie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,972,694 A * | 10/1999 | Mathus ............... B01L 3/50255 422/534 |
| 5,981,268 A | 11/1999 | Kovacs et al. |
| 6,033,628 A | 3/2000 | Kaltenbach et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Muller et al. |
| RE37,977 E | 2/2003 | Sugihara et al. |
| 6,535,822 B2 | 3/2003 | Mansky et al. |
| 6,536,499 B2 | 3/2003 | Voorhees et al. |
| 6,566,079 B2 | 5/2003 | Hefti |
| 6,573,063 B2 | 6/2003 | Hochman |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| D515,220 S | 2/2006 | Miller et al. |
| 6,998,249 B1 | 2/2006 | McKim et al. |
| 7,010,347 B2 | 3/2006 | Schecter |
| 7,148,059 B1 | 12/2006 | Tillotson et al. |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,476,827 B1 | 1/2009 | Bhullar et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadter et al. |
| 7,876,108 B2 | 1/2011 | Abassi et al. |
| D631,976 S | 2/2011 | Oonuma et al. |
| 8,026,080 B2 | 9/2011 | Wang et al. |
| 8,041,515 B2 | 10/2011 | Wang et al. |
| 8,206,903 B2 | 6/2012 | Wang et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,673,628 B2 | 3/2014 | Schroeder et al. |
| D705,944 S | 5/2014 | Chang et al. |
| D717,968 S | 11/2014 | Klein et al. |
| 8,916,357 B2 | 12/2014 | Abassi et al. |
| 8,921,041 B2 | 12/2014 | Wang et al. |
| 9,200,246 B2 | 12/2015 | Thomas et al. |
| 9,279,797 B2 | 3/2016 | Clements et al. |
| 9,399,787 B2 | 7/2016 | Abassi et al. |
| D784,549 S | 4/2017 | Brooks et al. |
| 9,612,234 B2 | 4/2017 | Li et al. |
| 9,625,472 B2 | 4/2017 | Xu et al. |
| 9,709,548 B2 | 7/2017 | Wang et al. |
| D817,509 S | 5/2018 | McMullin et al. |
| 10,012,636 B2 | 7/2018 | Wang et al. |
| 10,067,121 B2 | 9/2018 | Abassi et al. |
| 10,533,985 B2 | 1/2020 | Wang et al. |
| D889,679 S | 7/2020 | White et al. |
| 2002/0010492 A1 | 1/2002 | Donovan et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge et al. |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0091397 A1 | 5/2004 | Picard |
| 2004/0106095 A1 | 6/2004 | Thomson et al. |
| 2004/0146849 A1 | 7/2004 | Huang et al. |
| 2004/0152067 A1 | 8/2004 | Wang et al. |
| 2005/0014130 A1 | 1/2005 | Liu et al. |
| 2005/0051723 A1 | 3/2005 | Neagle et al. |
| 2005/0112544 A1 | 5/2005 | Xu et al. |

(56) References Cited

U.S. PATENT DOCUMENTS

| | | |
|---|---|---|
| 2005/0153425 A1 | 7/2005 | Xu et al. |
| 2005/0182447 A1 | 8/2005 | Schecter |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer et al. |
| 2006/0216203 A1 | 9/2006 | Fuller et al. |
| 2006/0240490 A1 | 10/2006 | Lee |
| 2006/0252054 A1 | 11/2006 | Lin et al. |
| 2007/0042347 A1 | 2/2007 | Rosen et al. |
| 2007/0087333 A1 | 4/2007 | Gruters et al. |
| 2007/0172939 A1 | 7/2007 | Xu et al. |
| 2007/0212423 A1 | 9/2007 | Epstein et al. |
| 2007/0281908 A1 | 12/2007 | Liang et al. |
| 2008/0190783 A1 | 8/2008 | Hyland |
| 2008/0286750 A1 | 11/2008 | Xu et al. |
| 2009/0017465 A1 | 1/2009 | Xu |
| 2009/0142790 A1 | 6/2009 | Fang et al. |
| 2009/0155821 A1 | 6/2009 | Kunich et al. |
| 2009/0241698 A1 | 10/2009 | Biksacky |
| 2009/0325213 A1 | 12/2009 | Gambari et al. |
| 2010/0029506 A1 | 2/2010 | Wang et al. |
| 2010/0202925 A1 | 8/2010 | Sonnleitner |
| 2011/0039294 A1 | 2/2011 | Wang et al. |
| 2011/0231103 A1 | 9/2011 | Fang |
| 2011/0300569 A1 | 12/2011 | Li et al. |
| 2012/0142031 A1 | 6/2012 | Xu et al. |
| 2012/0295253 A1 | 11/2012 | Abassi et al. |
| 2012/0322050 A1 | 12/2012 | Abassi et al. |
| 2013/0025347 A1 | 1/2013 | Rhodes et al. |
| 2013/0123136 A1 | 5/2013 | Abassi et al. |
| 2013/0143254 A1* | 6/2013 | Thomas ........... G01N 33/54373 435/297.5 |
| 2014/0203818 A1 | 7/2014 | Wang et al. |
| 2015/0125894 A1 | 5/2015 | Laing et al. |
| 2015/0177236 A1 | 6/2015 | Van Praet et al. |
| 2015/0185206 A1 | 7/2015 | Abassi et al. |
| 2015/0218549 A1 | 8/2015 | Li et al. |
| 2015/0231634 A1 | 8/2015 | Szita et al. |
| 2015/0260642 A1 | 9/2015 | Papin et al. |
| 2015/0362476 A1 | 12/2015 | Clements et al. |
| 2016/0195563 A1 | 7/2016 | Oonuma et al. |
| 2016/0258931 A1 | 9/2016 | Silva et al. |
| 2016/0327500 A1* | 11/2016 | Koo ................... G01N 15/1031 |
| 2017/0205391 A1 | 7/2017 | Li et al. |
| 2017/0269062 A1 | 9/2017 | Abassi et al. |
| 2017/0315131 A1 | 11/2017 | Xu et al. |
| 2017/0370907 A1 | 12/2017 | Abassi et al. |
| 2018/0217146 A1 | 8/2018 | Varadarajan et al. |
| 2018/0246079 A1 | 8/2018 | Wang et al. |
| 2018/0313758 A1 | 11/2018 | Hsieh et al. |
| 2019/0195861 A1 | 6/2019 | Abassi et al. |
| 2019/0204250 A1 | 7/2019 | Van Ingelgem et al. |
| 2021/0301245 A1 | 9/2021 | Li et al. |

FOREIGN PATENT DOCUMENTS

| | | |
|---|---|---|
| EP | 1195432 B1 | 6/2004 |
| EP | 1040345 B1 | 3/2006 |
| EP | 2213721 A1 | 8/2010 |
| EP | 2291645 A1 | 3/2011 |
| WO | 1996/001836 A1 | 1/1996 |
| WO | 1999/066329 A1 | 12/1999 |
| WO | 2000/037628 A1 | 6/2000 |
| WO | 2000/070343 A2 | 11/2000 |
| WO | 2000/071669 A1 | 11/2000 |
| WO | 2001/025769 A2 | 4/2001 |
| WO | 2001/038873 A2 | 5/2001 |
| WO | 2001/079529 A1 | 10/2001 |
| WO | 2002/004943 A2 | 1/2002 |
| WO | 2002/042766 A2 | 5/2002 |
| WO | 2003/0016887 A2 | 2/2003 |
| WO | 2004/010103 A2 | 1/2004 |
| WO | 2005/005979 A1 | 1/2005 |
| WO | 2005/04 7 482 A2 | 5/2005 |
| WO | 2005/077104 A2 | 8/2005 |
| WO | 2006/017762 A2 | 2/2006 |
| WO | 2006051387 A1 | 5/2006 |
| WO | 2009/137440 A1 | 11/2009 |
| WO | 2010/129725 A1 | 11/2010 |
| WO | 2011/146531 A1 | 11/2011 |
| WO | 2012/043820 A1 | 4/2012 |
| WO | 2014/085727 A1 | 6/2014 |
| WO | 2016164857 A1 | 10/2016 |
| WO | 2016/183143 A1 | 11/2016 |
| WO | 2017/068421 A1 | 4/2017 |
| WO | 2017/087945 A1 | 5/2017 |
| WO | 2018200995 A2 | 11/2018 |
| WO | WO-2018200995 A2 * | 11/2018 ............ B01L 3/5055 |
| WO | 2018223142 A1 | 12/2018 |
| WO | 2019028122 A1 | 2/2019 |
| WO | 2019029122 A1 | 2/2019 |
| WO | 2019094230 A1 | 5/2019 |
| WO | 2019165119 A1 | 8/2019 |

OTHER PUBLICATIONS

Neher, Erwin, "Molecular Biology Meets Microelectronics." Nature Biotechnology, 2001; 19:114.

Nerurkar et al. "The Use of Surfactants to Enhance the Permeability of Peptides Through Caco-2 Cells by Inhibition of an Apically Polarized Efflux System." Pharmaceutical Research, 1996, 13(4):528-534.

Nicolazzi et al. "Cationic Lipids for Transfection." Current Medicinal Chemistry, 2003, 10:1263-1277.

Oka et al. "A New Planar Multielectrode Array for Extracellular Recording: Application to Hippocampal Acute Slice." Journal of Neuroscience Methods, 1999, 93:61-67, Elsevier Science, B.V.

Pancrazio et al. "Portable Cell-Based Biosensor System for Toxin Detection." Sensors and Actuators 1998; 53:179-185.

Patolsky et al. "Detection of Single-Base DNA Mutations by Enzyme-Amplified Electronic Transduction." Nature Biotechnology, 2001, 19:253-257.

Pethig et al. "Positive and Negative Dielectrophoretic Collection of Colloidal Particles Using Interdigitated Castellated Microelectrodes." Applied Physics, 1992, 24:881-888.

Qiu et al. "Real-Time Monitoring Primary Cardiomyocyte Adhesion Based on Electrochemical Impedance Spectroscopy and Electrical Cell-Substrate Impedance Sensing" Analytical Chemistry, 2008, 80:990-996.

Rabow et al. "Mining the National Cancer Institute's Tumor-Screening Database: Identification of Compounds with Similar Cellular Activities." Journal of Medicinal Chemistry, 2002, 45:818-840.

Richards et al. "A Modified Microchamber Method for Chemotaxis and Chemokinesis." Immunological Communications, 1984, 13(1):49-62.

Rishpon et al. "An Amperometric Enzyme-channeling Immunosensor." Biosensors & Bioelectronics, 1997, 12(3):195-204.

Slaughter et al. "Artificial Neural Network for Temporal Impedance Recognition of Neurotoxins." 2006 International Joint Conference on Neural Networks 2006; Jul. 16-21, 2001-2008.

Sohn et al. "Capacitance Cytometry: Measuring Biological Cells One by One." Proceedings of the National Academy Of Sciences, 2000, 97{20}:10687-10690.

Steinem et al. "Impedance and Shear Wave Resonance Analysis of Ligand-Receptor Interactions at Functionalized Surfaces and of Cell Monolayers." Biosensors & Bioelectronics, 1997, 12(8):787-808.

Stenger et al. "Detection of Physiologically Active Compounds Using Cell-Based Biosensors." Trends in Biotechnology, 2001; 19(8):304-309.

Svetlicic et al. "Charge Displacement by Adhesion and Spreading of a Cell." Bioelectrochemistry, 2000, 53:79-86.

Wang et al. "Selective Dielectrophoretic Confinement of Bioparticles in Potential Energy Wells." Applied Physics, 1993, 26:1278-1285.

(56) References Cited

OTHER PUBLICATIONS

Wang et al. "Dielectrophoretic Manipulation of Cells with Spiral Electrodes." Biophysical Journal, 1997, 72:1887-1899.
Wang et al. "Separation of Polystyrene Microbeads Using Dielectrophoretic/Gravitational Field-Flow-Fractionation." Biophysical Journal, 1998, 74:2689-2701.
Warburg "Ueber die Polarisationscapacitat des Platins." Annals of Physics, 6:125-135 (1901).
Wegener et al. "Electric Cell-Substrate Impedance Sensing (ECIS) as a Noninvasive Means to Monitor the Kinetics of Cell Spreading to Artificial Surfaces." Experimental Cell Research 2000; 259:158-166.
Wegener et al., Use of Electrochemical Impedance Measurements to Monitor Beta-Adrenergic Stimulation of Bovine Aortic Endothelial Cells. European Journal of Physiology, 437:925-934 (1999).
Wolf et al. "Monitoring of Cellular Signalling and Metabolism with Modular Sensor-Technique: The PhysioControl-Microsystem (PCM)." Biosensors and Bioelectronics 1998; 13:501-509.
Xiao et al. "Assessment of Cytotoxicity Using Electric Cell-Substrate Impedance Sensing: Concentration and Time Response Function Approach." Analytical Chemistry, 2002, 74:5748-5753.
Xiao et al. "An In-Depth Analysis of Electric Cell-Substrate Impedance Sensing to Study the Attachment and Spreading of Mammalian Cells." Analytical Chemistry, 2002; 74 (6):1333-1339.
Xiao et al. "On-Line Monitoring of Cell Growth and Cytotoxicity Using Electric Cell-Substrate Impedance Sensing (ECIS)." Biotechnology Progress, 2003; 19:1000-1005.
Xing et al. "Dynamic Monitoring of Cytotoxicity on Microelectronic Sensors" Chemical Research in Toxicology., 2005, 18 (2):154-161.
Yamauchi et al. "Spatially and Temporally Controlled Gene Transfer by Electroporation into Adherent Cells on Plasmid DNA-Loaded Electrodes." Nucleic Acids Research, 2004, 32(22):1-8.
Yu et al. "Real-Time Monitoring of Morphological Changes in Living Cells by Electronic Cell Sensor Arrays: An Approach To Study G Protein-Coupled Receptors." Analytical Chemistry, 2006, 78:35-43.
Automated Cell Monitoring Instrument. Applied BioPhysics, 2002, [retrieved from the internet] http://www.biophysics.com/pages/front.html, 1 page.
Cell Migration Studies with TECAN Systems. TECAN., Sep. 1999, [retrieved from the internet] http://www.ecan.com/migration_introl.pdf, 10 pgs.
Detect Cell Migration and Invasion in a Homogeneous Fluorescent Assay System. BD Biosciences, http://www.bdbiosciences.com/discovery_labware/Products/inserts/BD_Falcon_HTS_fluoroblok_inserts ndividual_fluoroblok_inserts/index.html, 2004.
HP 4284A Precision LCR Meter Operation Manual, Aug. 1998, Hewlett Packard, 6th Edition, pp. 1-460.
Molecular Viewer New Products page. Science 298:2409 (2002).
CA2556219 Office Action mailed Aug. 9, 2010.
CA2575573 Office Action mailed Apr. 4, 2012.
EP05722991 Extended European Search Report mailed Apr. 3, 2009.
EP11193882 Extended European Search Report mailed Apr. 5, 2012.
PCT/US2018/020817 International Search Report and Written Opinion mailed May 7, 2018.
PCT/US2021/24035 International Search Report and Written Opinion mailed Jun. 29, 2021.
Agilent Technologies, Inc. "Agilent Introduces Revolutionary Real-Time Cell Analyzer", published Aug. 23, 2019, pp. 1-11 ; https:/lwww.labbulletin.com/articles/agilent-introduces-revolutionary-real-time-cell-analyzer.
Translation of WO2018200995A2, Veiseh Mandana, Nov. 1, 2018 (Year: 2018).
EP13171137 Extended European Search Report mailed Aug. 16, 2013.

Wang et al. "Electronic Manipulation of Cells on Microchip-Based Devices." In Biochip Technology {eds), 2001, pp. 149-177, Harwood Academic Publishers, PA, USA.
Wang et al. "A Theoretical Method of Electrical Field Analysis for Dielectrophoretic Electrode Arrays Using Green's Theorem." Journal of Physics D: Applied Physics, 1996; 29:1649-1660.
Yang et al. "Cell Separation on Microfabricated Electrodes Using Dielectrophoretic/Gravitational field-flow Fractionation." Analytical Chemistry, 1999, 71:911-918.
Yang et al. "A Novel Microfluidic Impedance Assay for Monitoring Endothelin-Induced Cardiomyocyte Hypertrophy." Biosensors and Bioelectronics, 2006, 22:1688-1693.
Neuro Probe A-Series {AA96, AB96, AC96) [retrieved from the internet] http://www.neuroprobe.com/protocol/pt_96a.html, 5 pgs.
EP09743420 European Search Report mailed Dec. 3, 2012.
PCT/US2009/033801 International Search Report and Written Opinion mailed Oct. 30, 2009.
Aravanis et al. "A Genetically Engineered Cell-Based Biosensor for Functional Classification of Agents" Biosensors & Bioelectronics, 2001, 16:571-577.
Banach et al. "Development of Electrical Activity in Cardiac Myocyte Aggregates Derived from Mouse Embryonic Stem Cells" Amerocam Journal of Physiology-Heart Circulatoy Physiology, 2003, 284: H2114-H2123.
Berdondini et al. "High-Density Electrode Array for Imaging in Vitro Electrophysiological Activity." Biosensors and Bioelectronics, 2005, 21:167-174.
Bergveld, P. "A Critical Evaluation of Direct Electrical Protein Detection Methods." Biosensors & Bioelectronics. 5:55-72 (1991).
Bieberich et al. "Neuronal Differentiation and Synapse Formation of PC12 and Embryonic Stem Cells on Interdigitated Microelectrode Arrays: Contact Structures for Neuron-to-Electrode Signal Transmission (NEST)" Biosensors and Bioelectronics 2004; 19:923-931.
Blagbrough et al. "Polyamines and Novel Polyamine Conjugates Interact with DNA in Ways That Can Be Exploited in Non-Viral Gene Therapy." Biochemical Society Transactions, 2003, 31, Part 2, pp. 397-406.
Bonetta, Laura. "The Inside Scoop-Evaluating Gene Delivery Methods." Nature Methods, Nov. 2005, 2(11):875-883.
Burns et al. "Neutrophil Transendothelial Migration is Independent of Tight Junctions and Occurs Preferentially at Tricellular Comers." Journal of Immunology, 1997, 2893-2903.
Cady et al. "Electrical Impedance Measurements: Rapid Method for Detecting and Monitoring Microorganisms," Journal of Clinical Mirobiology, 1978; 7(3):265-272.
Cartellieri et al. "Chimeric Antigen Receptor-Engineered T Cells for Immunotherapy of Cancer." Journal of Biomedicine and Biotechnology, 2010, 1-13.
Chang et al. "Impedimetric Monitoring of Cell Attachment on Interdigitated Microelectrodes." Sensors and Actuators, 15 2005, B 105:159-163.
Ciambrone et al. "Cellular Dielectric Spectroscopy: A Powerful New Approach to Label-Free Cellular Analysis." Journal of Biomolecular Screening, 2004, 9(6):467-480.
Connolly et al. "An Extracellular Microelectrode Array for Monitoring Electrogenic Cells in Culture," Biosensors and Biolectronics, 1190, 5:223-234.
Duan et al. "Separation-Free Sandwich Enzyme Immunoassays Using Microporous Gold Electrodes and Self-Assembled Monolayer/ Immobilized Capture Antibodies." Analytical Chemistry, 1994, 66:1369-1377.
Ehret et al. "Monitoring of Cellular Behaviour by Impedance Measurements on Interdigitated Electrode Structures." Biosensors and Bioelectronics 1997; 12(1):29-41.
Ehret et al. "On-Line Control of Cellular Adhesion with Impedance Measurements Using Interdigitated Electrode Structures", Medical & Biological Engineering & Computing, 1998; 36:365-370.
Falk et al. "A 48-well Micro Chemotaxis Assembly for Rapid and Accurate Measurement of Leukocyte Migration." Journal of Immunological Methods., 1980, 33:239-247.
Fuhr et al. "Positioning and Manipulation of Cells and Microparticles Using Miniaturized Electric Field Traps and Travelling Waves." Sensors and Materials 7(2):131-146 (1995).

(56) References Cited

OTHER PUBLICATIONS

Giaever et al, "Monitoring Fibroblast Behavior in Tissue Culture with an Applied Electric Field." Proceedings of the National Academy of Sciences. USA; 1984; 81(Jun.):3761-3764.
Gutmann et al. "Evidence for Different ABC-Transporters in Caco-2 Cells Modulating Drug Uptake." Pharmaceutical Research, 1999, 16(3):402-407.
Hadjout et al. "Automated Real-Time Measurement of Chemotactic Cell Motility." Bio Techniques, 2001, 31:1130-1138.
Hapala, Ivan. "Breaking the Barrier: Methods for Reversible Permeabilization of Cellular Membranes." Critical Reviews in Biotechnology, 1997, 17(2):105-122.
Hescheler et al. "Determination of Electrical Properties of ES Cell-derived Cardiomyocytes Using MEAs." Journal of Electrocardiology, 2004, vol. 37, Suppl.
Hidalgo et al. "Characterization of the Human Colon Carcinoma Cell Line (Caco-2) as a Model System for Intestinal Epithelial Permeability," Gastroenterology, 1989; 96:736-749.
Horvath et al. "Monitoring of Living Cell Attachment and Spreading Using Reverse Symmetry Waveguide Sensing." Applied Physics Letters, 2005, 86:071101.
Huang et al. "Dielectrophoretic Cell Separation and Gene Expression Profiling on Microelectronic Chip Arrays." Analytical Chemistry, 2002, 74:3362-3371.
Keese et al. "Real-time Impedance Assay to Follow the Invasive Activities of Metastatic Cells in Culture." BioTechniques, 2002, 33:842-850.
Klauke et al. "Extracellular Recordings of Field Potentials from Single Cardiomyocytes." Biophysical Journal, Oct. 2006, 91 :2543-2551.
Kleinman et al. "Basement Membrane Complexes with Biological Activity." Biochemistry 1986; 25(2):312-318.
Kloß et al. "Microcavity Array (MCA)-Based Biosensor Chip for Functional Drug Screening of 3D Tissue Models." Biosensors and Bioelectronics, 2008, 23:1473-1480.
Kowolenko et al. "Measurement of Macrophage Adherence and Spreading with Weak Electric Fields." Journal of Immunological Methods, 1990; 127:71-77.
Larsen et al. "Somatic Cell Counting with Silicon Apertures." Micro Total Analysis Systems, 2000, 103-106.
Lin et al. "Electroporation Microchips for In Vitro Gene Transfection." Journal of Micromechanics and Microengineering, 2001, 11 :542-547.
Lin et al. "Simulation and Experimental Demonstration of the Electric Field Assisted Electroporation Microchip for In Vitro Gene Delivery Enhancement." Miniaturisation for Chemistry, Biology & Bioengineerin., 2004, 4:104-108.
Lo et al. American Physical Society March Meeting 2010, Portland Oregon, vol. 55, No. 2, Poter Session Abstract, BAPS, Mar. 2010 C1 268.
Lo et al. "Monitoring Motion of Confluent Cells in Tissue Culture." Experimental Cell Research 1983; 204:102-109.
Lo et al. "Impedance Analysis of Mock Cells Measured by Electric Cell-Substrate Impedance Sensing." Biophysical Journal, 1995, 69:2800-2807.
Lo et al. "pH Changes in Pulsed CO2 Incubators Cause Periodic Changes in Cell Morphology." Experimental Cell Research, 1994, 213:391-397.
Loffert et al. "Multiplex PCR with QIAGEN: Taq DNA Plymerase and PCR Buffer." QIAGENews, 1994, 4:15-18.
Luan et al. "Clustering of Time-Course Gene Expression Data Using a Mixed-Effects Model with B-Splines." Bioinformatics, 2003, 19(4):474-482.
Luong et al. "Monitoring Motility, Spreading, and Mortality of Adherent Insect Cells Using an Impedance Sensor.", Analytical Chemistry, 2001, 73(8):1844-1848.
Mitra et al. "Electric Measurements Can Be Used to Monitor the Attachment and Spreading of Cells in Tissue Culture." Biotechniques, 1991, 11(4):504-510.
Miyata et al. "New Wound-Healing Model Using Cultured Corneal Endothelial Cells." Japan Journal of Opthalmology, 1990, 34:257-266.
EP05786773 Extended European Search Report mailed Mar. 21, 2013.
EP05852157 Extended European Search Report mailed Sep. 13, 2011.
EP058122680 Extended European Search Report mailed Sep. 7, 2011.
EP03748948 Extended European Search Report mailed Mar. 12, 2007.
EP10772804.0 Extended European Search Report mailed Oct. 27, 2017.
PCT/US2009/042787 International Search Report and Written Opinion mailed Jun. 24, 2009.
PCT/US2011/036877 International Search Report mailed Sep. 2, 2011.
PCT/US2013/072439 International Search Report mailed Feb. 19, 2014.
PCT/US2005/034561 International Preliminary Report on Patentability mailed Mar. 27, 2007.
PCT/US2005/034561 International Search Report mailed Sep. 27, 2006.
PCT/US2005/027943 International Preliminary Report on Patentability mailed Apr. 11, 2007.
PCT/US2005/027943 International Search Report and Written Opinion mailed Mar. 21, 2007.
PCT/US2004/037696 International Search Report mailed May 16, 2005.
PCT/US2005/04481 International Search Report mailed Sep. 12, 2005.
PCT/US2016/063066 ISR and WO mailed Jan. 30, 2017.
PCT/US2018/044774 ISR and WO mailed Oct. 23, 2018.
Batalov et al. "Differentiation of Cardiomyocytes from Human Pluripotent Stem Cells Using Monolayer Culture." Biomarkers Insights, 2015, 10(s1):71-76.
Brustaert et al. "Cardiac Endothelial-Myocardial Signaling: Its Role in Cardiac Growth, Contractile Performance, and Rhythmicity." Physiological Reviews, 2003, 83:59-115.
Jacot et al. "Substrate Stiffness Affects the Functional Maturation of Neonatal Rat Ventricular Myocytes." Biophysics Journal, Oct. 2008, 95:3479-3487.
Lundy et al. "Structural and Functional Maturation of Cardiomyocytes Derived from Human Pluripotent Stem Cells." Stem Cells and Development, 2013, 22(14):1991-2002.
McDevitt et al. "In Vitro Generation of Differential Cardiac Myofibers on Micropatterned Laminin Surfaces." Journal of Biomedical Materials Research, 2002, 60:472-479.
Moran et al. "Temporal Trends in Ischemic Heart Disease Mortality in 21 World Regions, 1980 to 2010 The Global Burden of Disease 2010 Study." Circulation, Apr. 8, 2014, 129(14):1483-1492.
Sathaye et al. "Electrical Pacing Counteracts Intrinsic Shortening of Action Potential Duration of Neonatal Rat Ventricular Cells in Culture." Journal of Molecular and Cellular Cardiology, 2006, 41 :633-641.
Takahashi et al. "Introduction of Pluripotent Stem Cells from Mouse Embryonic and Adult Fibroblast Cultures by Defined Factors." Cell, Aug. 25, 2006, 126:663-676.
Takahashi et al. "Introduction of Pluripotent Stem Cells from Adult Human Fibroblasts by Defined Factors." Cell, Nov. 30, 2007, 131:861-872.
Werley et al. "Geometry-dependent functional changes in iPSC-derived cardiomyocytes probed by functional maging and RNA Sequencing." PLOS One, Mar. 23, 2017, 12{3):e0172671.
Yang et al., "Tri-iodo-L-Thyronine Promotes the Maturation of Human Cardiomyocytes-Derived from Induced Dluripotent Stem Cells." Journal of Molecular Cell Cardiology, Jul. 2014, 72:296-304.
Zimmermann et al. "Tissue Engineering of a Differentiated Cardiac Muscle Construct." Circulation Research, Feb. 8, 2002, 90:223-230.
Maher et al. "Targeting Cytotoxic T Lymphocytes for Cancer Immunotherapy." British Journal of Cancer, 2004, 91:817-821.

(56) References Cited

OTHER PUBLICATIONS

EP16867327.5 Supplementary Partial European Search Report mailed Jun. 6, 2019.
Carrega et al. "Susceptibility of Human Melanoma Cells to Autologous Natural Killer (NK) Cell Killing: HLA-Related Effector Mechanisms and Role of Unlicensed NK Cells." PLoS One, Dec. 4, 2009, 4(12):e8132.
Peper et al. "An Impedance-Based Cytotoxicity Assay for Real-Time and Label-Free Assessment of T-Cell-Mediated Killing of Adherent Cells," Journal of Immunological Methods, Jan. 29, 2014, 405:192-198.
Oberg et al. "Monitoring Circulating gamma-delta-T Cells in Cancer Patients to Optimize gamma-delta-T Cell-Based Immunotherapy." Frontiers in Immunology, Dec. 17, 2014, 5(643):1-7.
Erskine et al. "Determining Optimal Cytotoxic Activity of Human Her2neu Specific CD8 T Cells by Comparing the CR51 Release Assay to the xCELLigence System," Journal of Visualized Experiments, Aug. 8, 2012, 66(e3683):1-6.
Alici et al. "Autologous Antitumor Activity by NK Cells Expanded from Myeloma Patients Using GMP-Compliant Components," Blood, Mar. 15, 2008, 111(6):3155-3162.
Label-Free Assay for NK Cell-Mediated Cytolysis, Jan. 1, 2013, pp. 1-8, retrieved from the internet May 23, 2019, URL discloses a method of assessing the effect of e.g. NK cell-mediated cytolysis on target cells using a cell substrate impedance monitoring devices indentical to the one used in the application as filed.
"xCELLigence System Application Table of Contents," Jan. 1, 2014, retrieved from the internet May 23, 2014, URL:hllps://www.ols-bio.de/media/pdf/Application_Book_09082014_OLS_xs.pdf.
Lamarche et al. Using Impedance-Based Approaches for Measuring Cell-Mediated Cytotoxicity and Antibody-Dependent Cell-Mediated Cytotoxicity (ADCC), Journal of Immuno Therapy of Cancer, Nov. 4, 2015, 3(Suppl 2):P214.
Baumann et al., "Microelectronic Sensor System for Microphysiological Application on Living Cells", Sensors and Actuators, 1999: 77 -89.
Becker et al. "Separation of Human Breast Cancer Cells from Blood by Differential Dielectric Affinity." Cell Biology, 1995, 92:860-864.
Berens et al. "The Role of Extracellular Matrix in Human Astrocytoma Migration and Proliferation Studied in a Microliter Scale Assay." Clinical and Experimental Metastasis, 1994; 12(6):405-415.
Burnett et al. "Fluorescence Imaging of Electrically Stimulated Cells." Journal of Biomolecular Screening 2003; 8(6):660-667.
Fusenig et al. "The Need for a Worldwide Consensus for Cell Line Authentication: Experience Implementing a Mandatory Requirement at the International Journal of Cancer". PLOS Biologiy, Apr. 17, 2017, 15(4) p. e2001438, pp. 1-13.
Giaever et al. "Micromotion of Mammalian Cells Measured Electrically." Proceedings of the National Academy of Sciences, USA, 1991; 88(Sepl.):7896-7900.
Henning et al. "Approach to a Multiparametric Sensor-Chip-Based Tumor Chemosensitivity Assay," Anti-Cancer Drugs 2001; 12:21-32.
Hug, Thomas, "Biophysical Methods for Monitoring Cell-Substrate Interactions in Drug Discovery." Assay and Drug Development Technologies, 2003; 1(3):1-10.
Ong et al. "Remote Query Resonant-Circuit Sensors for Monitoring of Bacteria Growth: Application to Food Quality Control." Sensors 2002; 2:219-232.
Simpson et al. "Whole-Cell Biocomputing." Trends in Biotechnology, 2001, 19(8):317-323.
Tiruppathi et al. "Electrical Method for Detection of Endothelial Cell Shape Change in Real Time: Assessment of Endothelial Barrier Function." Proceedings of the National Academy of Sciences, USA, 1992, 89:7919-7923.
Wang et al. "Cell Separation by Dielectrophoretic Field-Flow-Fractionation." Analytical Chemistry., 2000, 72:832-839.

\* cited by examiner

SYSTEMS AND METHODS FOR ELECTRONICALLY AND OPTICALLY MONITORING BIOLOGICAL SAMPLES

CROSS REFERENCE TO RELATED APPLICATIONS

This application is a division of U.S. Nonprovisional application Ser. No. 16/833,651, filed Mar. 29, 2020. The contents of the aforementioned application are hereby incorporated by reference in its entirety.

TECHNICAL FIELD

The invention relates generally to systems and methods for electronically and optically monitoring biological samples and more specifically to systems and methods that electronically and optically monitor a same biological sample continuously in real time in a single well.

BACKGROUND OF THE INVENTION

Cell based assays provide a preliminary evaluation of the effects of therapeutics on human biology. While many cell-based assays are endpoint assays, which are a limited to a single point in time, a technology known as cell-substrate impedance monitoring permits continuous monitoring of cells. Cell-substrate impedance monitoring assesses the interaction between cells and electrodes, where changes in cell attachment, growth, morphology and motility over electrodes results in a detectable change. To this end, cell-substrate impedance monitoring is a powerful tool to assess cell proliferation and cytolysis.

While cell-substrate impedance monitoring technology can reveal the kinetics of cell responses to potential therapeutics, it has its limitations. In particular, it is limited to detecting changes that occur to the cells as they are cultured on the electrode surface. Therefore, there is a need to develop further advances that expand the ability of cell-substrate impedance monitoring to evaluate the effects of therapeutics on cell biology.

BRIEF SUMMARY OF THE INVENTION

In one aspect of the invention a system for electronically and optically monitoring biological samples is provided, the system including: a multi-well plate having a plurality of wells configured to receive a plurality of biological samples, each of the wells having a set of electrodes and a transparent window on a bottom surface of the well that is free of electrodes; an illumination module configured to illuminate the wells; a cradle configured to receive the multi-well plate, the cradle having an opening on the bottom that is configured to expose the transparent windows of the wells; and an optical imaging module movable across different wells of a same multi-well plate to capture images through the windows via the open bottom. In some embodiments the set of electrodes are configured for monitoring cell-substrate impedance.

Although the illumination module can be a single light, preferably the illumination module includes a plurality of lights configured to independently illuminate one or more of the wells. More preferably, the illumination module includes a light emitting diode (LED) array. Most preferably, each LED is arranged to illuminate a single well. In preferred embodiments, the illumination module is a bright field illumination module.

The cradle is configured to receive and preferably cover the multi-well plate and thus can provide a hinged cover. Preferably the illumination module is joined to the inner surface of the cover. The cradle can include a contact sensor that senses receipt of the plate. In some embodiments, the cradle electronically engages both the multi-well plate for electronic communication with the sets electrodes and the illumination module for communicating illumination instructions.

Since the open bottom of the cradle exposes the transparent windows of the wells, the optical imaging module can be positioned underneath the cradle and configured to move from well to well to capture images through corresponding transparent windows. In some embodiments, the optical imaging module is configured to capture one or more images from a single well at a time. In some embodiments, images are captured under bright field illumination of well(s), such as for determining cell counts or a cell confluence parameter (e.g. percent confluence). In other embodiments, images, such as fluorescence images, are captured after molecule excitation. The optical imaging system can itself include an excitation light source configured to excite one or more molecules, such as fluorescent molecules conjugated to antibodies or antibody fragments for binding to biological molecules such as proteins, polypeptides or nucleic acids, inside cells or on cell surfaces. Examples of excitation light sources can include one or more lights selected from the group consisting of an ultraviolet light, a violet light, a blue light, a green light, a yellow light, an orange light, and a red light.

In some embodiments, the optical imaging module includes a camera capable of capturing a series of cell images consecutively at sufficiently short time intervals for showing cell motion. In some embodiments the camera captures at least 30 images per second. In other embodiments the camera captures at least 60 images per second. In either or both embodiments, the optical imaging module can include the camera, a bandpass filter, a tube lens, and an objective lens. High-speed imaging not only permits cell movement to be shown visually but also permits superimposing images from different light sources (e.g. bright field illumination and multiple light sources of different wavelengths each for exciting fluorescent molecules to produce a-single-color fluorescence image) revealing cell changes occurring during movement. In some embodiments, the captured images from bright field illumination and three or more color fluorescence are superimposed to form a single image for each time point. From this imaging, a cell count or a cell parameter can be determined as well as absence or presence of fluorescence, total fluorescence intensity, and average fluorescence intensity, which further reveals detailed cell kinetics.

The system can also include or be coupled with computer processor communicatively coupled to: the cradle for selectively operating each of the sets of electrodes, optionally for electronically monitoring cell-substrate impedance within one or more wells; the illumination module for selectively illuminating the one or more wells; and the optical imaging module for its selective movement and capturing and receiving images from the one or more wells. In some embodiments, the computer processor is programmed to capture images from the one or more wells via the optical imaging module in response to the one or more wells reaching or following a set impedance-based value or parameter from the electronic monitoring. In some embodiments, the computer processor is configured to electronically monitor cell-substrate impedance and optically monitor a same well and is configured to pair impedance and optical data for display or analysis. In some embodiments, the computer processor is configured to electronically monitor cell-substrate impedance over a time period including specific time interval between two consecutive electronic impedance measurements/monitoring; and optically monitor a same well over a period that is within the time period for electronic monitoring or over a different time period from electronic monitoring. Impedance monitoring time period can be programmed to be as short as minutes to as long as hours, days or even weeks. Impedance monitoring time interval(s) between two consecutive impedance measurements can be specified or programmed as short as seconds or less than a second, to as long as one minute, multiple minutes, one hour even multiple hours. Optical monitoring periods can be programmed inside, outside or over the same time period as the one or more impedance monitoring time period.

While the system can be used with a single plate, the system can also include two additional multi-well plates, each having a plurality of wells configured to receive a plurality of samples, each of the wells having a set of electrodes and a transparent window on a bottom surface of the well that is free of electrodes; two additional illumination modules configured to illuminate the wells of the two additional multi-well plates; and two additional cradles configured to receive the two additional multi-well plates, the two additional cradles each having an open bottom that exposes the transparent windows of the wells of two additional multi-well plates; and where the optical imaging module is movable across all wells to capture images through all windows via the exposed bottoms.

The system can also include a cell or tissue culture vessel that is not configured for electronic monitoring, where the optical imaging module is configured to capture images within the cell or tissue culture vessel. As an exemplary embodiment, the system can include a multi-well plate having a plurality of wells configured to receive a plurality of biological samples, each of the wells having a transparent bottom surface; an illumination module configured to illuminate the wells; a cradle configured to receive the multi-well plate, the cradle having an opening on the bottom that is configured to expose all of the transparent bottom surfaces of the wells; and an optical imaging module movable across different wells of a same multi-well plate to capture images through the windows via the exposed bottoms.

In a related aspect of the invention, a method of monitoring cells is provided, which includes electronically monitoring cells within wells of a multi-well plate, each of the wells having a set of cell-substrate impedance monitoring electrodes, and a transparent window on a bottom surface of the well that is free of electrodes; and capturing images through the transparent window from at least one well that is being electronically monitored. In some embodiments, the images are captured regularly at a fixed time interval between two consecutive image capturing or irregularly over a time period within the electronic monitoring time period, the method optionally including capturing the images at a same time interval between two consecutive image capturing as the time interval between two consecutive electronic measurements of the cells.

In some embodiments, prior to the step of capturing images from the at least one well, the electronic monitoring outputs a result from the at least one well that meets a set value, which instructs the optical imaging module to capture the images from the at least one well. Examples of set values can include predetermined impedance-based values.

In some embodiments, the images being captured are bright field images of the cells. In such embodiments the method can also include counting cells from the bright field images and optionally deriving cell confluence numbers or parameters (e.g. percent confluence) from the bright field images.

In other embodiments, the captured images include fluorescence images of the cells. In such embodiments, the method can include determining a fluorescence parameter from the images, optionally selected from one or more of the group consisting of total fluorescence counts, total fluorescence intensity, and average fluorescence intensity. The fluorescence parameters are calculated or determined separately for fluorescent images of each color, for example, blue, green and red colors.

In still other embodiments, the images being captured include bright field images of the cells and fluorescence images of the cells. In such embodiments, the method also includes deriving cell confluence numbers or parameters from the bright field images and optionally counting cells from the bright field images; determining a fluorescence parameter from the fluorescence images, optionally selected from one or more of the group consisting of total fluorescence counts, total fluorescence intensity, and average fluorescence intensity; and optionally, superimposing the bright field images and fluorescence images of one or more colors for one or more of the wells.

In a related aspect, a method of monitoring cells is provided, which includes electronically monitoring cells within wells of a multi-well plate over a time period, each of the wells having a set of cell-substrate impedance monitoring electrodes, and a transparent window on a bottom surface of the well that is free of electrodes; and capturing images through the transparent window over a time period that is within or outside of the time period for electronic monitoring. The time period used for electronic monitoring may be the same as the time period used for image capturing, or different from that used for image capturing. These time periods for electronic monitoring and optical monitoring can be specified or programmed as short as less than one minute, to as long as hours, days or even weeks. Over the time period of electronic monitoring, electronic monitoring can be continuous at a specified, fixed time interval between two consecutive electronic measurements. Optic monitoring can be continuous over the time period at a specified, fixed time interval between two consecutive image capturing. These time intervals can be specified or programmed as short as seconds or less than a second, to as long as one minute, multiple minutes, one hour even multiple hours.

In some embodiments, the images being captured are bright field images of the cells. In such embodiments the method can also include counting cells from the bright field images and optionally deriving cell confluence numbers or parameters (e.g. percent confluence) from the bright field images.

In other embodiments, the captured images include fluorescence images of the cells. In such embodiments, the method can include determining a fluorescence parameter from the images, optionally selected from one or more of the group consisting of total fluorescence counts, total fluorescence intensity, and average fluorescence intensity. The fluorescence parameters are calculated or determined separately for fluorescent images of each color, for example, blue, green and red colors.

In still other embodiments, the images being captured include bright field images of the cells and fluorescence images of the cells. In such embodiments, the method also includes deriving cell confluence numbers or parameters from the bright field images and optionally counting cells from the bright field images; determining a fluorescence parameter from the fluorescence images, optionally selected from one or more of the group consisting of total fluorescence counts, total fluorescence intensity, and average fluorescence intensity; and optionally, superimposing the bright field images and fluorescence images of one or more colors for one or more of the wells.

DETAILED DESCRIPTION OF PREFERRED EMBODIMENTS

Figure 1A:
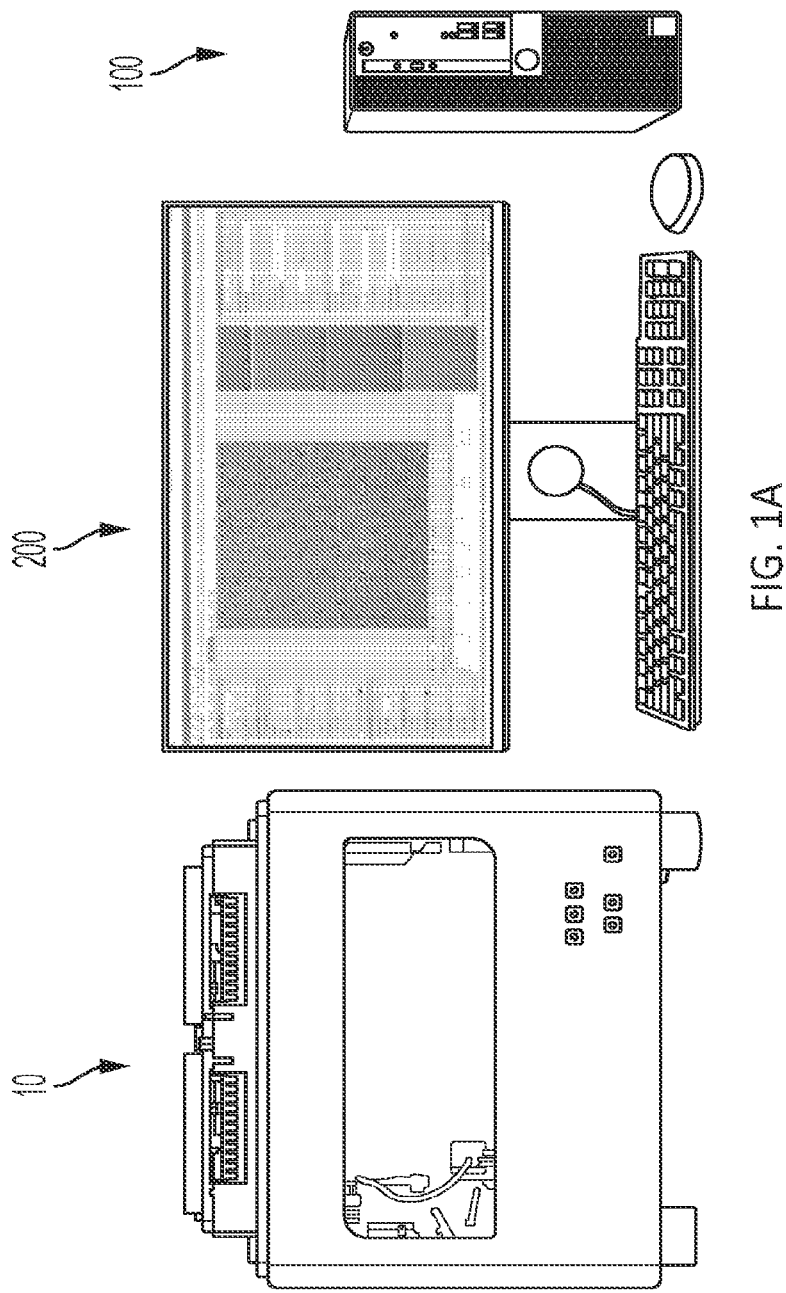
FIG. 1A is a photograph of exemplary system 10 for electronically and optically monitoring biological samples, where an optional user interface 200 is displaying cell imaging data.

The systems and methods described herein enable cell health and behavior to be monitored continuously, and in the same well, from the very different perspectives, namely, from real-time electronic monitoring and live cell imaging. The streamlined workflow, high reproducibility, and quantitative kinetics of the system makes it ideal for a wide range of cell-based assays, including but not limited to, cell health monitoring, proliferation, cytotoxicity, apoptosis, immune cell killing, cell receptor activation, cell differentiation including stem cell differentiation.

The continuous nature of the systems and methods have two major advantages. In contrast to endpoint assays that provide mere snapshots of a process, real-time tracking ensures that important phenomena do not get missed. Secondly, the continuous nature of the technical approach dramatically reduces that amount of hands-on time required to run an assay. Once cells have been seeded and any treatments added, no further involvement is necessary.

The systems and methods are preferably used to assess biological samples or effects on cells. The cells can be primary cells isolated from any species or can be cells of cell lines. The cells can be genetically engineered cells. For example, these include cells from a genetically modified organism, such as for example from a "gene knockout" organism, or cells that have been engineered to over-express an endogenous gene or a transgene, or cells whose normal gene expression has been manipulated (e.g. by use of antisense molecules or silencing RNA.), cells that have been modified by CRISPR and/or other gene editing technologies, or cells that have been engineered to express therapeutic proteins such as CHO cells.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Nonlimiting examples of electrode structure units are interdigitated electrode structure units and concentric electrode structure units. Additional examples of electrode structures may also include a pair of a small measurement/recording electrode (e.g. microelectrode of circular shape having a diameter between a size as small as less than 10 microns and a size larger as large as 100, or a few hundred microns), and a much larger reference electrode. Multiple small recording electrodes—forming a microelectrode array, may share a common reference electrode. Such recording electrodes can be used for conducting extracellular recording, by amplifying and recording electrical voltage signals between small recording electrodes and much larger reference electrodes. In extracellular recording embodiments, an extracellular recording system (including voltage signal amplifier and other electronic hardware circuitry for measuring electrical voltage plus signal processing algorithm implemented in software and/or firmware) is used rather than an impedance measurement system (e.g., impedance analyzer system, including electronic hardware circuitry measuring electrical current and voltage, and signal and data processing algorithm in software and/or firmware).

As used herein, an "electrode bus" is a portion of an electrode that connects individual electrode elements or substructures. An electrode bus provides a common conduction path from individual electrode elements or individual electrode substructures to another electric connection. In the devices of the present invention, an electrode bus can contact each electrode element of an electrode structure and provide an electrical connection path to electrical traces that lead to a connection pad.

As used herein, "electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

As used herein, a "connection pad" is an area on an apparatus or a device (e.g. multi-well plate), which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

As used herein, "interdigitated" means having projections coming one direction that interlace with projections coming from a different direction in the manner of the fingers of folded hands (with the caveat that interdigitated electrode elements preferably do not contact one another).

As used herein, "electrodes (or electrode structures) have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10.

As used herein, "detectable change in impedance between or among electrodes" (or "detectable change in impedance between or among electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among electrodes" does not require the impedance change at all frequencies being detectable. "Detectable change in impedance between or among electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode (typically referred to as a "counter electrode"). is significantly smaller than the impedance change due to cell attachment or growth on the smaller electrode (typically referred to as a "working electrode" or a "measuring electrode"). Ordinarily, the ratio of surface area between the largest electrode and the smallest electrode is more than 10. Preferably, the ratio of surface area between the largest electrode and the smallest electrode is more than 20, 30, 40, 50 or 100. Examples where "at least two electrodes have substantially different surface area" include the "Electronic Cell-Substrate Impedance Sensing (ECIS)" approach developed by Giaver and Keese.

As used herein, "arranged in a row-column configuration" means that, in terms of electric connection, the position of an electrode, an electrode array or a switching circuit is identified by both a row position number and a column position number.

A "Cell Index" or "CI" is a parameter that can derived from measured impedance values and that can be used to reflect the change in impedance values. There are a number of methods to derive or calculate Cell Index. CI has been explained previously at length, such as in U.S. Pat. Nos. 8,344,742; 7,470,533; 7,192,752; PCT/US03/22557 and elsewhere. Each is herein incorporated by reference in its entirety. A "Normalized Cell Index" at a given time point is calculated by dividing the Cell Index at the time point by the Cell Index at a reference time point. Thus, the Normalized Cell Index is 1 at the reference time point. "Normalized Cell Index" has been explained previously at length, such as in U.S. Pat. Nos. 8,344,742; 7,470,533; 7,192,752; PCT/US03/22557 and elsewhere. Each is herein incorporated by reference in its entirety. A "delta cell index" at a given time point is calculated by subtracting the cell index at a standard time point from the cell index at the given time point. Thus, the delta cell index is the absolute change in the cell index from an initial time (the standard time point) to the measurement time. "Delta cell index" been explained previously at length, such as in U.S. Pat. Nos. 8,344,742; 7,470,533; 7,192,752; PCT/US03/22557 and elsewhere. Each is herein incorporated by reference in its entirety. A "Cell Change Index" or "CCI" is a parameter derived from Cell Index and "CCI" at a time point is equal to the $1^{st}$ order derive of the Cell Index with respect to time, divided by the Cell Index at the time point. "CCI" been explained previously at length, such as in U.S. Pat. Nos. 8,344,742; 7,470,533; 7,192,752; PCT/US03/22557 and elsewhere. Each is herein incorporated by reference in its entirety.

As used herein, "dose-response curve" means the dependent relationship of response of cells on the dose concentration of a test compound. The response of cells can be measured by many different parameters. For example, a test compound is suspected to have cytotoxicity and cause cell death. Then the response of cells can be measured by percentage of non-viable (or viable) cells after the cells are treated by the test compound. Plotting this percentage of non-viable (or viable) cells as a function of the does concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present application is that in a single experiment, one can obtain "dose-response curves" at multiple time points since the system allows for the continuous monitoring of cells and provides impedance measurement at many time points over a time range as short as a few minutes to as long as days or weeks.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "each well contains . . . same type of cells" means that, for the intended purpose, each well contains same type of cells; it is not necessary that each well contains exactly identical type of cells. For example, if the intended purpose is that each well contains mammalian cells, it is permissible if each well contains same type of mammalian cells, e.g., human cells, or different mammalian cells, e.g., human cells as well as other non-human mammalian cells such as mice, goat or monkey cells, etc.

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, cell number, cell quality, cell cycling, etc.

An "impedance value" is the impedance measured for electrodes in a well with or without cell present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

As used herein, a "liquid (fluid) sample" refers to a sample that naturally exists as a liquid or fluid, e.g., a biological fluid. A "liquid sample" also refers to a sample that naturally exists in a non-liquid status, e.g., solid or gas, but is prepared as a liquid, fluid, solution or suspension containing the solid or gas sample material. For example, a liquid sample can encompass a liquid, fluid, solution or suspension containing a biological tissue.

As used herein, "sample" refers to anything which may contain a moiety to be isolated, manipulated, measured, quantified, detected or analyzed using apparatuses, microplates or methods in the present application. The sample is preferably a biological sample, such as a biological fluid or a biological tissue. Examples of biological fluids include suspension of cells in a medium such as cell culture medium, urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The biological samples may further include cell suspensions, solutions containing biological molecules (e.g. proteins, enzymes, nucleic acids, carbohydrates, chemical molecules binding to biological molecules).

A "test compound" is any compound whose activity or direct or indirect effect or effects on cells is investigated in any assay. A test compound can be any compound, including, but not limited to, a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown.

As an introduction, beginning at FIG. 1A, an exemplary system 10 configured for electronically and optically monitoring samples continuously in real time is shown in communication with a computer processor 100 loaded with software and user interface 200. By collecting and analyzing different and distinct streams of information from a single assay, the system 10 provides multiple vantage points for studying cellular activity. The information richness of this multiplex assay lies not merely in the number of parameters it reports, but also in the distinctness/uniqueness of the perspectives that it affords. The system 10 described herein enables cell health and behavior to be monitored simultaneously, and in the same well, from the very different perspectives of real-time cellular impedance and live cell imaging.

Figure 1B:
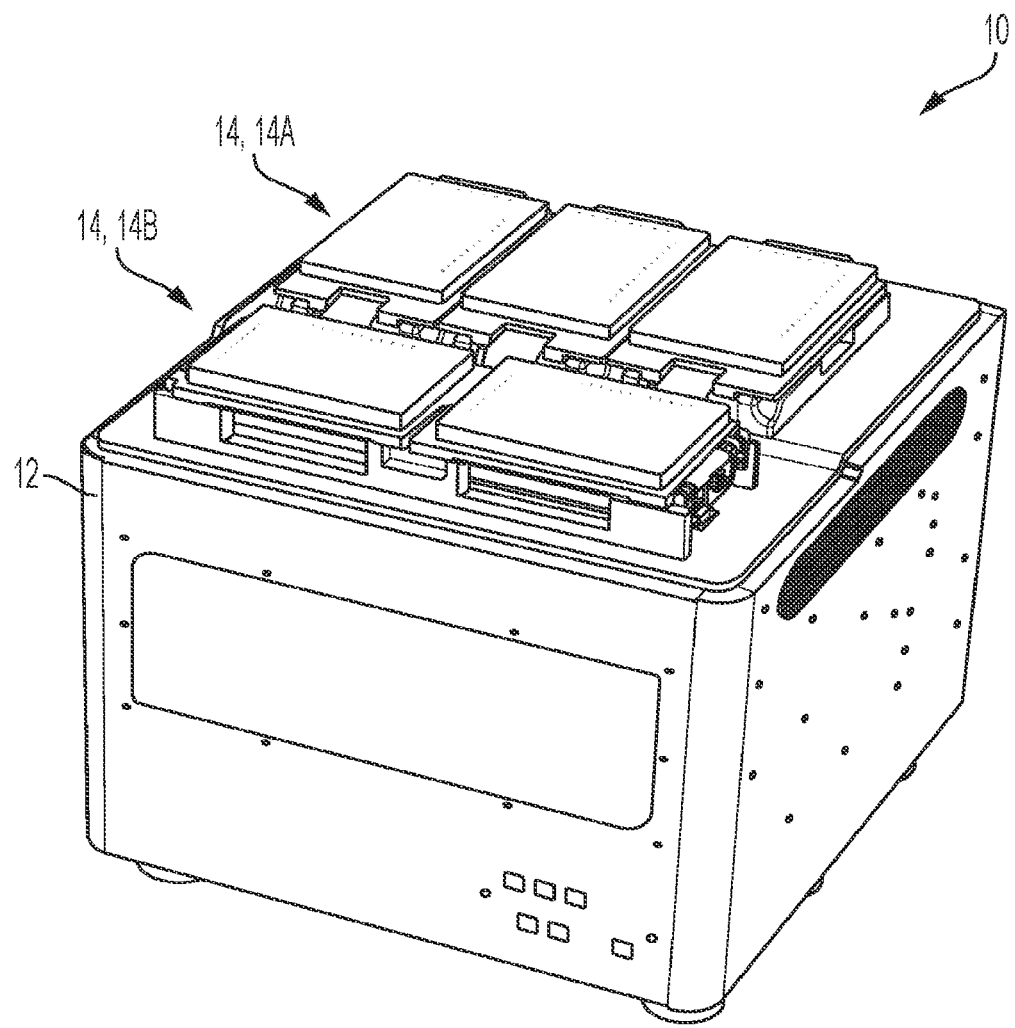
FIG. 1B depicts the primary housing 12 with five accessible cradles 14.

Moving onto FIG. 1B, the system 10 is preferably sized for placement in commercially available cell culture incubators for regulating temperature, CO2 and moisture conditions for cells. That is, the system 10 is sized for placement in a cell culture incubator so that the incubator rather than the system 10 regulates cell culturing conditions, such as temperature, CO2 and humidity. Though sizing can vary depending on the needs of the user, the system 10 shown in FIG. 1A and FIG. 1B has a footprint of about 430 mm×445 mm×410 mm.

The top of the primary housing 12 is embodied as a platform having five cradles 14, where three cradles 14A are for configured for electronically (e.g. cell-substrate impedance) and optically monitoring biological samples and two cradles 14B are for optically monitoring biological samples without electronic monitoring. While a total of five cradles 14 are shown, one of ordinary skill in the art would recognize that increasing the footprint of the system 10 may allow for additional cradles 14. In addition, one of ordinary skill in the art would recognize that it possible to have fewer cradles 14 (e.g. 4, 3, 2 cradles 14 or a single cradle 14) than those shown in FIG. 1, including the same or fewer "electronic" cradles 14A (e.g. 3, 2 or 1 cradle 14A) configured for both electronic and optical monitoring of biological samples and/or the same or less number of the "optical only" cradles 14B (e.g. 2 or 1) configured for only optical monitoring of biological samples.

Figure 2B:
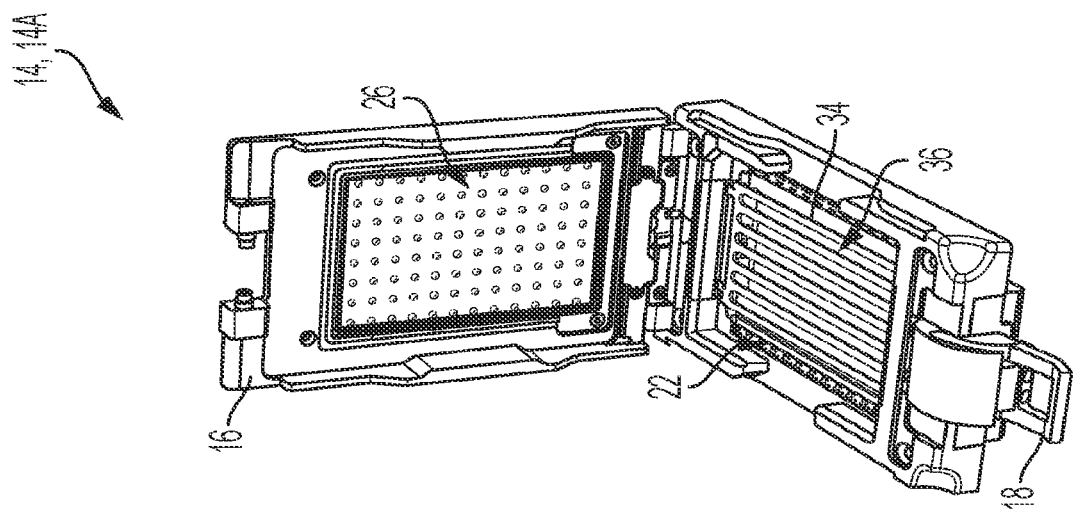
FIG. 2B shows a cradle 14 in an open configuration.
Figure 2A:
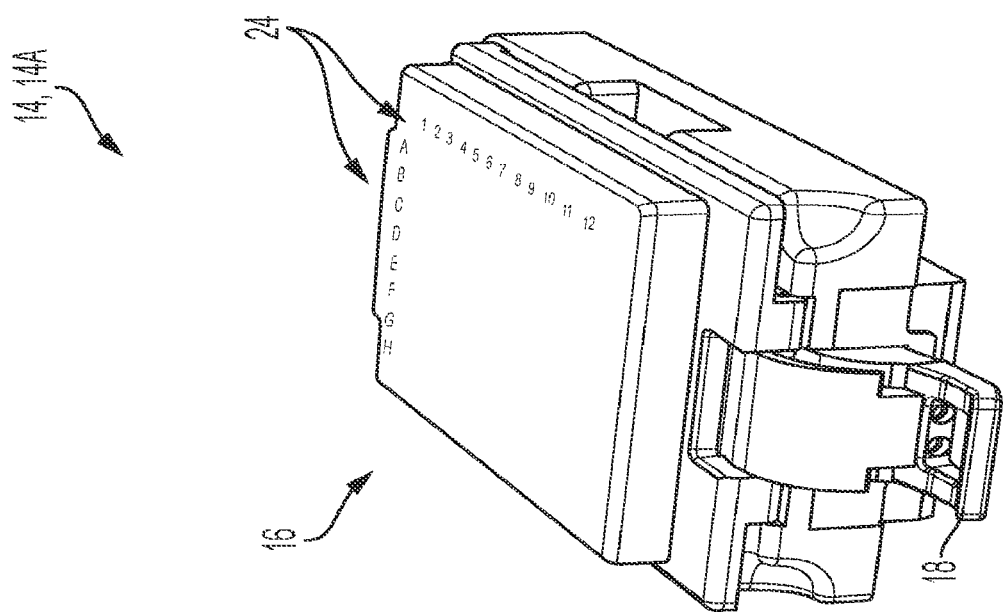
FIG. 2A shows the cradle 14 in a closed configuration.
Figure 2C:
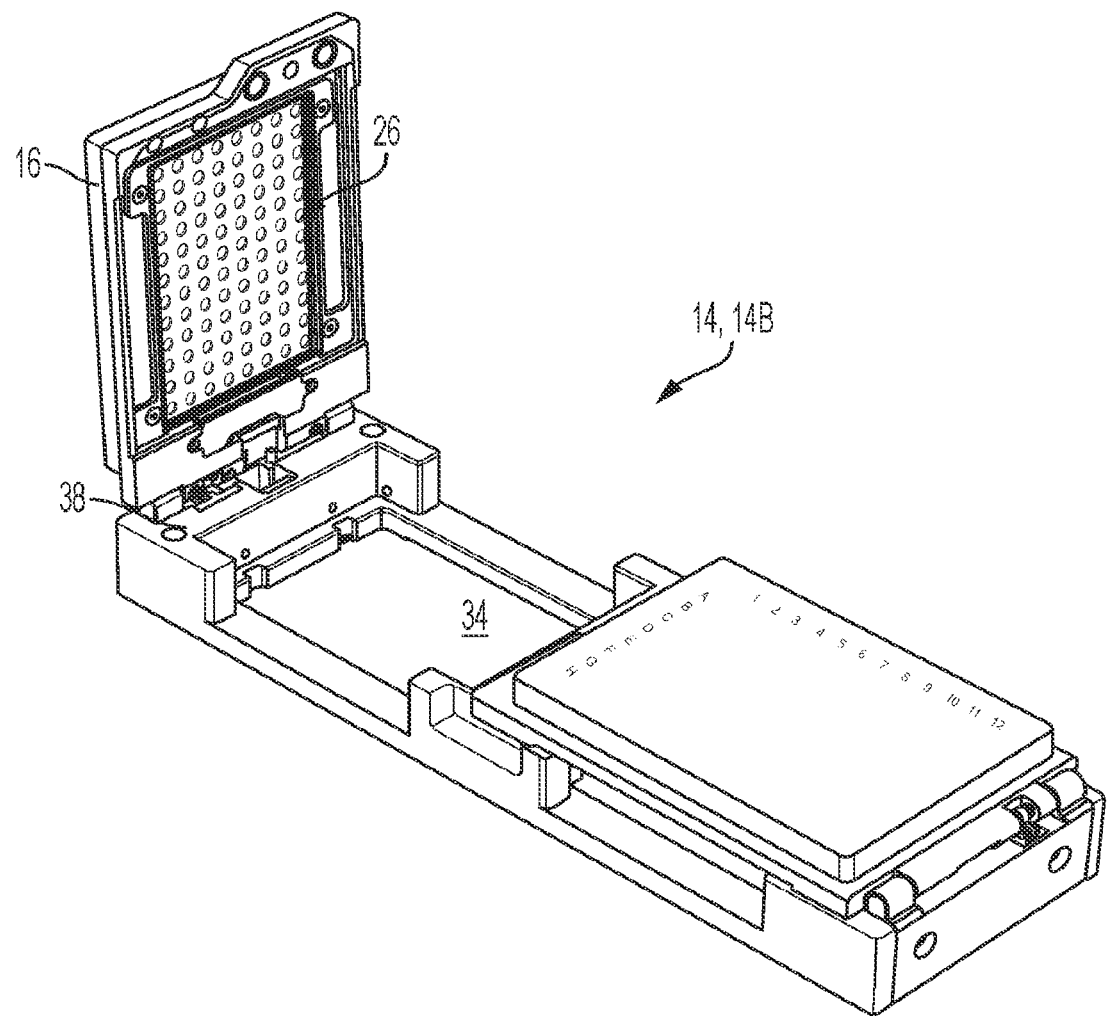
FIG. 2C shows a dual cradle 14 in open and closed positions.

As shown more clearly in FIGS. 2A-2C, each cradle 14A configured for electronic monitoring preferably has a hinged cover 16, which can be locked closed using a movable engagement handle 18. Locking the cover 16 closed ensures a snug fit for electric engagement between electronic plates 20 (see FIG. 4) and pogo pins 22 (see FIG. 2B), which connects to an impedance analyzer or impedance measurement circuitry for monitoring impedance inside the system 10, and ultimately communicate with the external computer processor 100 (FIG. 1A) for electronic monitoring. However, as shown in FIG. 2C, each cradle 14B configured solely for optical imaging does not require an electronic engagement between the plate and cradle components and thus does not require a mechanism for locking the cover 16 closed. In both instances, the outside of the hinged cover 16 can be marked with indicia 24 consistent with the intended format of the plate or vessel added to the cradle 14.

Figure 3:
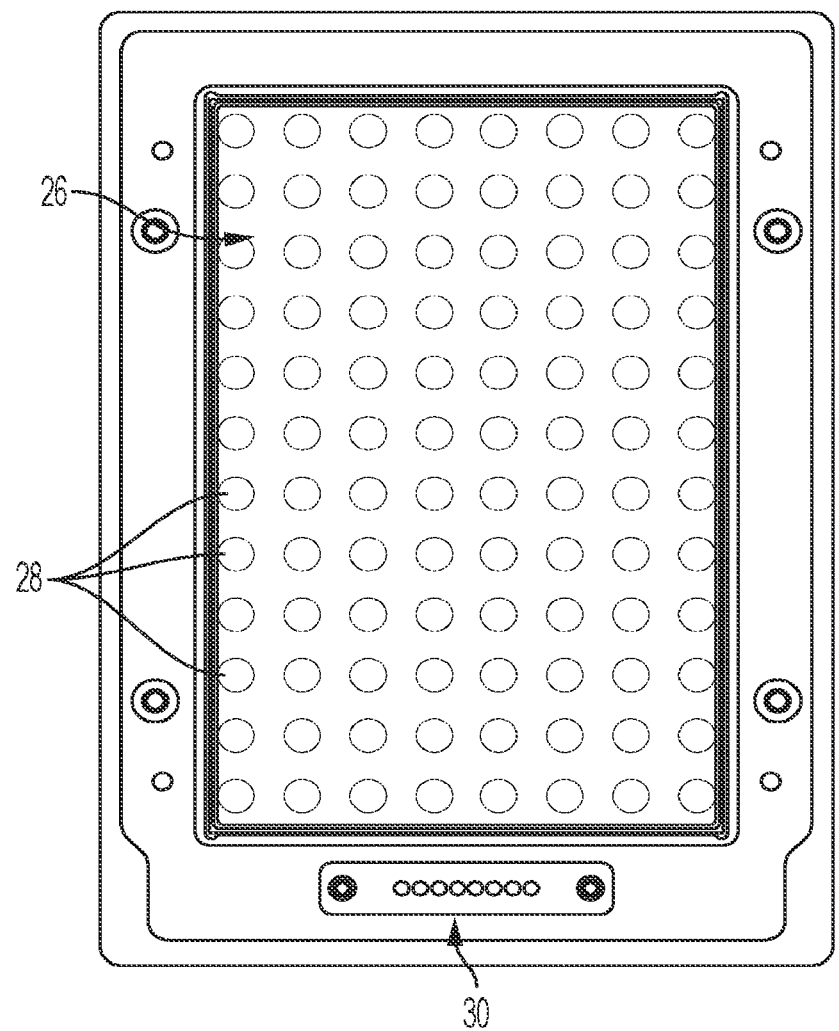
FIG. 3 shows a bright field illumination module 26 joined to a cradle cover 14.

Inside the cradle, preferably along the cover 16, is an illumination module 26 configured to illuminate the interior of the cradle 14. Better shown in FIG. 3, in preferred embodiments illumination module 26 is made up of a light emitting diode (LED) array, which itself is formed from a plurality of discrete LEDs 28 which receive instructions from the computer processor 100 (FIG. 1A) via electrical contacts 30. In some embodiments, LED arrays can be exchanged, such as for different multi-well formatted plates (e.g. 6 well, 12 well, 20 well, 48 well, 96 well, 384 well) or other culture vessels by way of screws. Preferably, each diode 28 is assigned to a single well 32 (See FIGS. 4-5) of a 96 well plate and thus configured to independently illuminate the corresponding well 32 for imaging. By providing diodes 28 immediately above the wells 32, the system 10 clearly illuminates the entire well 32 to ensure quality imaging. In preferred embodiments, the illumination module 26 is configured for bright field illumination, which means that the illumination module 26 emits white light. Consistent with conventional light microscopy, differences in the amount of white light passing through the biological sample provides sufficient contrast to identify cell components such as cell membrane, nucleus and other fine details depending on camera magnification and therefore may be used for cell counting and/or cell confluence analysis or to ensure cells are properly settled against the bottom of the well 32 prior to electronic monitoring. Imaging may be further enhanced by staining biological samples with image enhancing dyes that improve contrast or identification of live cells under bright field illumination (e.g. dead cells absorb Trypan Blue) to assess cytotoxicity, cell viability and/or cell proliferation.

Control over illumination is performed by way of the computer processor 100. To this end, the computer processor 100 may selectively illuminate one or more diodes 28 in response to results from electronic monitoring of the biological sample. For example, biological cells may be monitored using cell-substrate impedance monitoring to assess cell growth and upon reaching a set value or parameter indicative of an established cell monolayer or established cell population, the computer processor 100 may instruct illumination of one or more electronically monitored wells 32 using one or more LEDs 28 to capture cell images. Moreover, during an experimental treatment, such as administration of a test compound to assess its cytotoxicity, the computer processor 100 may selectively instruct illumination of one or more LEDs 28 at predefined time points or in response to changes in cell-substrate impedance monitoring for cell imaging to confirm a reduced population of cells. Still further, the computer processor 100 may instruct bright field illumination using one or more diodes 28 from the illumination module 26 to capture images simultaneously while conducting electronic monitoring (e.g. cell-substrate impedance monitoring).

Returning to FIG. 2B and FIG. 2C, white light passing through the biological sample ultimately exits the cradle 14 through its open bottom 34. By "open" it is meant that the bottom 34 is not completely opaque. As will be discussed in more detail in paragraphs that follow, this open bottom 34 exposes transparent windows (see FIG. 5) providing a path for capturing images. In embodiments configured for electronic monitoring of cells a slotted protective shield 36 may span the open bottom 34 for protection of pogo pins 22 especially during loading and unloading the multi-well plates 22 into or from the cradle 14, 14A.

For completeness, the development of cradle 14 adapted for electronic monitoring had to overcome challenges inherent to electronic measurement of cells using multi-well plates. For example, in conventional electronic monitoring of biological samples, vessels, such as multi-well plates adapted with electrodes require docketing stations that themselves have complex electrode-selection circuitry for communication with and switching the measurements to different sets of electrodes in different wells of the plates. Much of such circuitry for switching and selecting measurement electrodes had to be moved to provide the required opening and thus imaging through the bottom 34 of the cradle 14. For example, FIG. 2B, demonstrates the use pogo-pins 22 (120 shown for communication with a 96 well electronic plate 20) lining portions of the outer perimeter of the cradle 14. However, moving or rerouting this circuitry to form the needed opening affects the electrical characteristics of the system 10. In particular, elongating electric wires to move required electrode switching circuitry farther away from pogo-pins adds to the resistance of the system and may result in interference of electronic noises from other electrical parts (such as the circuitry for driving linear motion stage 66 and 70 in the system 10 of FIG. 8), which will ultimately affect the resolution and precision of electronic monitoring. This is especially important in the preferred electrode configurations, where all the wire resistances for switching and selecting each set of the electrodes across all the wells must be equal or about equal. In addition, another challenge with electronic monitoring of cells is that electrode switching circuitry increases local heat generation in the system 10, which was previously dissipated within each cradle under the docking station. Thus, moving or reconfiguring electrode switching/selection circuitry and wiring away from its conventional placement also affects heating of the system 10, which presented additional challenges in the development of such a system 10. Thus, achieving a system that is suitable for both electronic monitoring and optical imaging of samples in a same well required special engineering development of the system 10 so that the electrode switching and selection circuitry could be relocated within the system 10 without resulting excessive local heat generation and without affecting the performance of electronic monitoring.

Through a number of innovative engineering design steps, electrode switching and selection circuitry was arranged in the vicinity of the pogo-pins 22. The locations and orientations of the electrode switching chips were designed to maximize distances among the chips despite the small space available for minimizing local heat generation. In addition, a printed circuit board (PCB board) was designed with appropriate electric trace layouts on different layers of the electrical conduction planes to minimize the variation of the electrode resistance between the pogo pins 22 and circuit switching chips for each set of electrodes across all the wells on the multi-well plates. In addition, electrical signal wires/lines were designed in appropriate relationships relative to the electrical ground lines and electrical ground planes on the PCB board to minimize the electrical interface from other circuits in the system.

Now, with reference to FIGS. 2B and 2C, each cradle 14 can include a mechanical sensor 38 that when pressed, signals both receipt of a multi-well plate 20, and a closed cover 16. Upon signaling, the cradle 14 is ready for electronic and/or optical monitoring.

Figure 4:
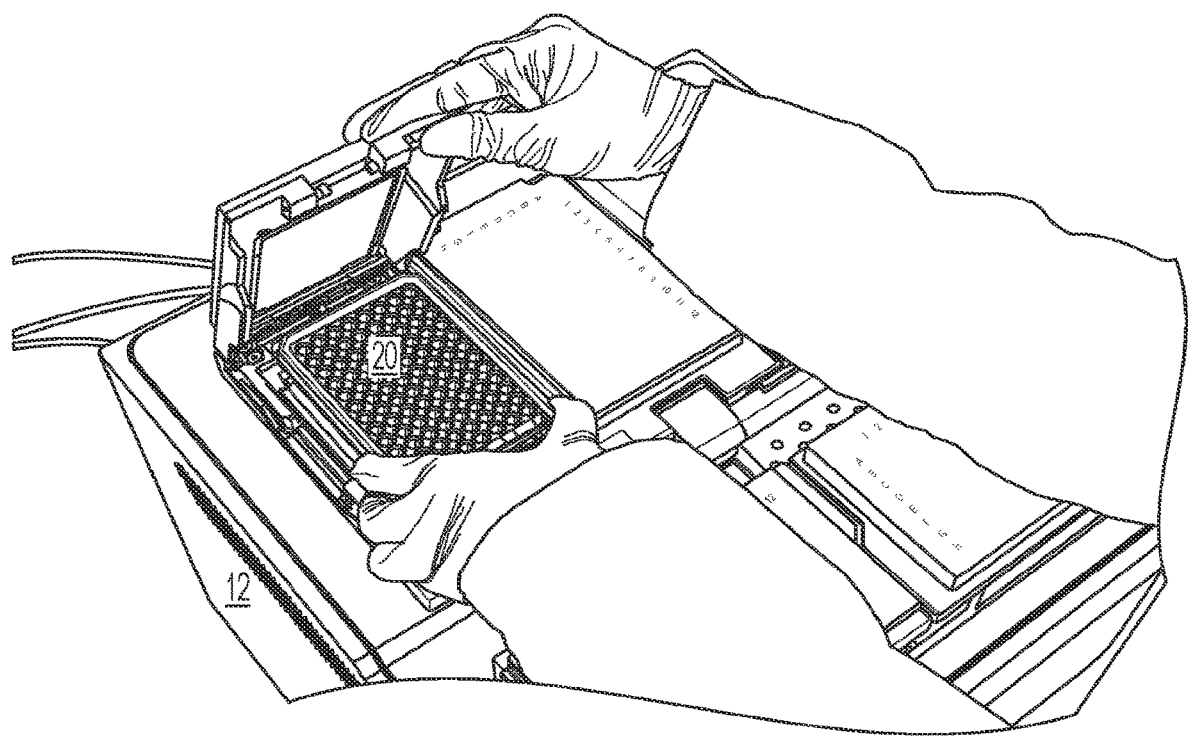
FIG. 4 depicts an exemplary multi-well plate 20.
Figure 5:
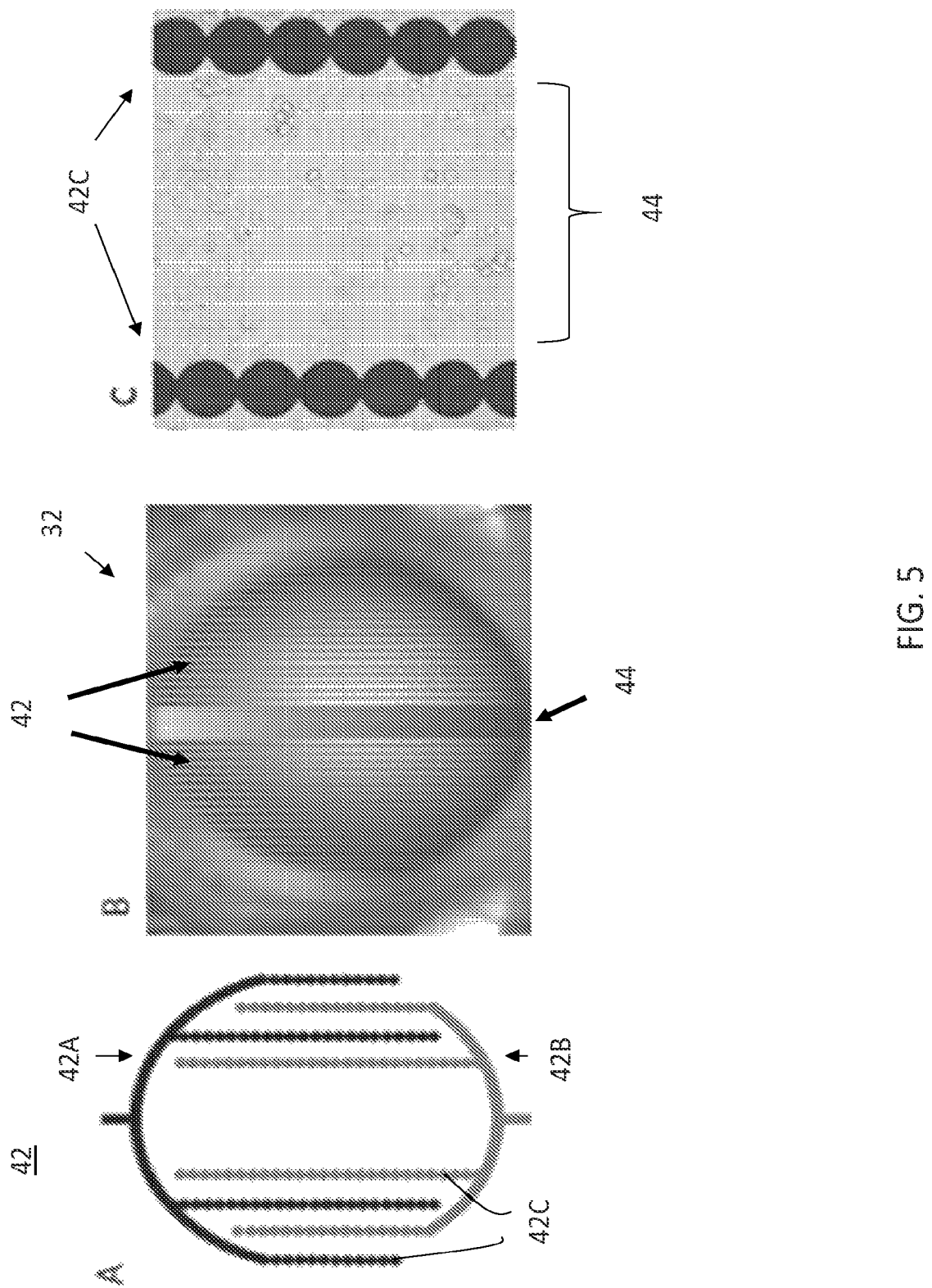
FIG. 5 is a photograph showing: a schematic of a set of electrodes 42 adapted for use with a centrally positioned transparent window 44 (Panel A); a photograph of a well 32 from a multi-well plate 20 (see FIG. 4) having a set of electrodes 42 on a bottom surface and a transparent window 44 that is free of electrodes 42 on the bottom surface (Panel B); and a captured image of cells through a transparent window 44 (Panel C).

Moving on to FIGS. 4-5, preferably each well 32 of electronic plates 20 has a set of electrodes 42 and a transparent window 44 that is free of electrodes 42 on a bottom surface of the well 32. By providing zones with electrodes 42 and a transparent zone free of electrodes 42, at least two distinctly different assays can be conducted in a single well 32. In particular, electronic monitoring (e.g. cell-substrate impedance monitoring) can be conducted using the set of electrodes 42 and optical imaging can be performed by focusing an optical imaging module 46 (FIG. 6) through the cradle open bottom 34 (see FIGS. 2B, 2C) and through the transparent window 44. A shown in FIG. 4, the electronic plates 20 are preferably multi-well plates 20, which can be described as having a "plurality of wells" configured for electric connection or electronic monitoring of a sample. The skilled artisan will appreciate that there may be one or more wells 32 in addition to these "plurality of wells" that do not have an electrical connection or are not for electronic monitoring. In such cases, wells 32 that lack electronic monitoring capabilities can serve as control wells or as "optical imaging only" wells 32. To this end, electronically monitoring wells 32 can be described as having a nonconducting substrate (e.g. bottom of the well); an electrode array defined by a set of electrodes 42 fabricated on the substrate; and a transparent viewing window 44 on the substrate that is free of electrodes 42.

The electrode 42 configuration can vary depending on the needs or desires of the user so long as the transparent window 44 for sample imaging can be retained. In some embodiments, the electrode array is a microelectrode array (MEA) consistent with the Electronic Cell-Substrate Impedance Sensing (ECIS) systems as described by Gaiver and Keese, where a single large reference electrode is paired with a plurality of small working or measuring electrodes. In ECIS, a small alternating current is applied across the electrode array. This results in a potential across the electrodes which is measured by the ECIS instrument. When cells are added to the ECIS Array and attach to the measuring electrodes, they act as insulators increasing the impedance. As cells grow and cover the measuring electrodes, the current is impeded in a manner related to the number of cells covering the electrode, the morphology of the cells, and the nature of the cell attachment. When cells proliferate or die, the impedance is altered.

An alternative and more preferred approach has been described previously (e.g. U.S. Pat. Nos. 8,344,742; 7,470,533; 7,192,752; and elsewhere, each of the listed patents is incorporated herein by reference in its entirety), where each electrode array includes two electrode structures 42A, 42B and each electrode structure 42A, 42B includes electrode elements 42C, but where innermost electrode elements 42C are removed to form the transparent window 44 (See schematic shown in FIG. 5, panel A). Electrode structures 42A, 42B are electrically coupled to connection pads or interfaces, which are located on an edge of the substrate and thus configured to electrically connect to pogo pins 22 on the cradle 14. Each electrode array has approximately uniform electrode resistance across the entire array. In contrast to the ECIS approach where significant changes in cell-substrate impedance are monitored at working or measuring electrodes only (not at large area reference electrodes), cell attachment or growth on any of the interdigitated electrodes impedes current in a detectable manner relating to the number of cells covering the electrode, the morphology of the cells and the nature of the cell attachment. That is, all electrodes 42 act as measuring or working electrodes in this configuration. Thus, the electrode array can be two or more electrode structures 42A, 42B that are constructed to have dimensions and spacing such that they can, when connected to a signal source, such as through the computer processor 100 and cradle 14, operate as a unit to generate an electrical field in the region of spaces around the electrode structures 42A, 42B.

When electronic monitoring is cell-substrate impedance monitoring electronic circuitry connects the sets of electrodes 42 to the computer processor 100 via the cradle 14. Preferably, in such embodiments the computer processor 100 communicates with impedance measurement circuitry or an impedance analyzer which may be fully incorporated within the system 10. The impedance analyzer may include electronic hardware circuitry measuring electrical current and voltage, and signal and data processing algorithm in firmware and/or software. The system 100, when connected to an impedance analyzer, can measure differences in impedance values that relate to cell behavior. For example, the system 10 can measure differences in impedance values when cells are attached to the electrode array and when cells are not attached to the electrode array, or can detect differences in impedance values when the number, type, activity, adhesiveness, or morphology of cells attached to the electrodes 42 change. In particular, cell-substrate impedance monitoring can reveal information about cell attachment or adhesion status (e.g. the degree of cell spreading, the attachment area of a cell, the degree of tightness of cell attachment, cell morphology) on the substrate including on the electrodes 42, cell growth or proliferation status; number of viable cells and/or dead cells in the well; cytoskeleton change and re-organization and number of cells going through apoptosis and/or necrosis.

In some embodiments, the impedance analyzer is capable of measuring impedance between 0.1 ohm and $10^5$ ohm in a frequency range of 1 Hz to 1 MHz. More preferably, the impedance analyzer is capable of measuring impedance between 0.1 ohm and $10^3$ ohm in a frequency range of 100 Hz to 100 kHz. The impedance analyzer is also preferably capable of measuring both resistance and reactance (capacitive reactance and inductive reactance) components of the impedance.

In addition, the system 10 includes electronic switches that can switch on and off connections to each of sets of electrodes 42 for selective monitoring. These switches are controlled by a software program preferably loaded into the computer processor 100. The software program directs connection of electrode arrays to the impedance analyzer and monitor cell-substrate impedance from the electrodes 42. During impedance monitoring, the impedance analyzer can monitor impedance at one frequency or at more than one frequency. Most often, impedance monitoring is performed at more than one time point for a given assay. Thus, the system can connect individual arrays to an impedance analyzer to monitor one, some, or all of the arrays at one or more time point. Further, the switches allow the selected individual arrays to be monitored in rapid succession for each desired monitoring time point. Each monitoring time point is in fact a narrow time frame (for example from a millisecond to minutes) of measurement in the assay during which impedance monitoring is performed. In some embodiments the software is programmable to direct impedance monitoring of any of the wells 32 of the plate 20 that include arrays at chosen time intervals.

In furtherance of the above, the system 10 can be used to efficiently and simultaneously perform multiple assays using circuitry to digitally switch from cell-substrate impedance monitoring over an array in one well 32 to cell-substrate impedance monitoring over an array in another well 32, whether from a same electronic plate 20 or another electronic plate 20. In some embodiments, the system under software control is capable of completing an impedance measurement for an individual well 32 at a single frequency within about one second or less. In further embodiments, cell-substrate impedance is monitored at millisecond (ms) resolution. Approaches for cell-substrate impedance monitoring at millisecond resolution can be found in U.S. Pat. Nos. 10,533,985, 10,012,636; 9,709,548; and elsewhere. Each of the listed patents is incorporated herein by reference in its entirety. Thus, in some embodiments, two sequential impedance measurements are monitored within 40 ms apart from one another. In some embodiments, two sequential impedance measurements are monitored within 20 ms apart from one another. In some embodiments, two sequential impedance measurements are monitored within 10 ms apart from one another. In some embodiments, two sequential impedance measurements are monitored within 1 ms apart from one another. In some embodiments, two sequential impedance measurements are monitored within less than 1 ms apart from one another.

While the system is described primarily with respect to cell-substrate impedance monitoring of cells, one of ordinary skill in the art would recognize that the system can also be adapted for conducting extracellular recording. Extracellular recording can be conducted by amplifying and recording electrical voltage signals between small recording electrodes and much larger reference electrodes (note that the use of such small recording electrodes and large reference electrode is similar to those used in ECIS). In extracellular recording embodiments, an extracellular recording system (including voltage signal amplifier and other electronic hardware circuitry for measuring electrical voltage plus signal processing algorithm implemented in software and/or firmware) is used rather than an impedance measurement system (e.g., impedance analyzer system, including electronic hardware circuitry measuring electrical current and voltage, and signal and data processing algorithm in software and/or firmware)

Figure 6:
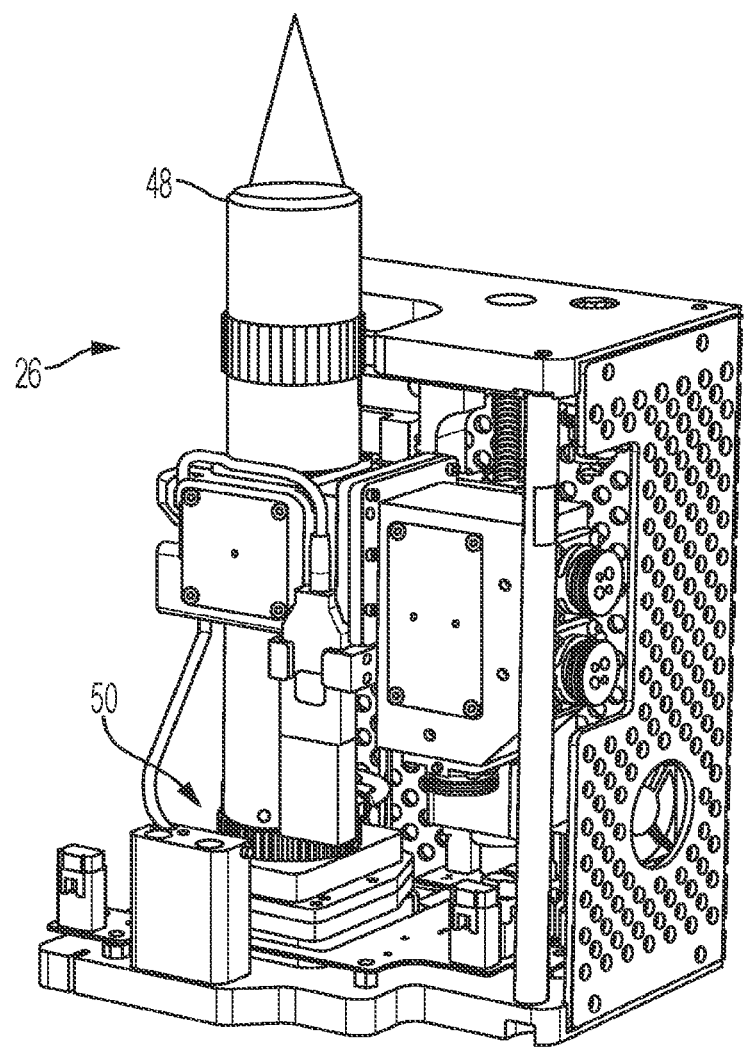
FIG. 6 shows an exemplary optical imaging module 26.
Figure 7:
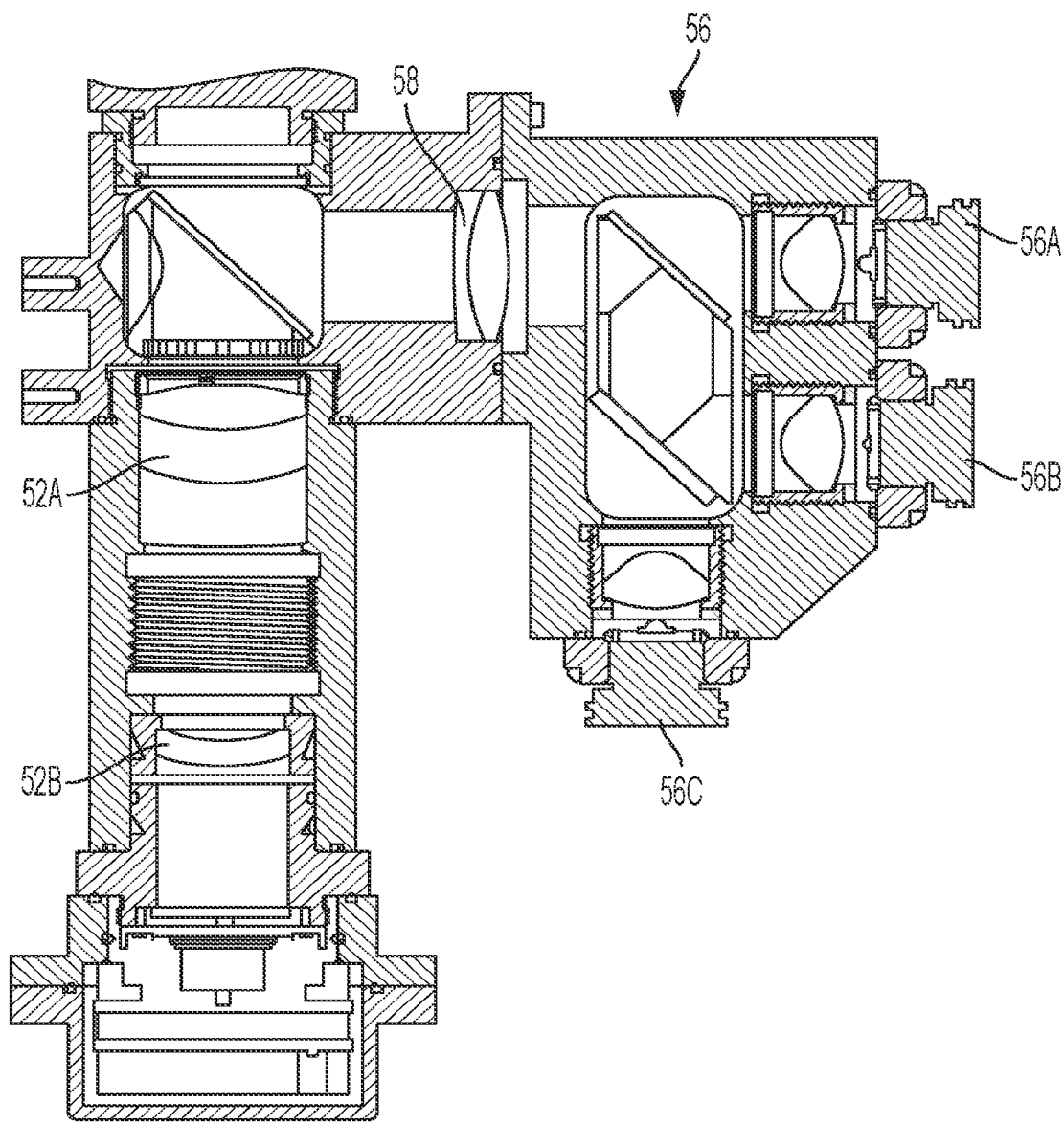
FIG. 7 is a cross-section of an exemplary optical imaging module 26.

Proceeding to FIGS. 6-7, an exemplary optical imaging module 26 is able to capture images from each well 32. In preferred embodiments, the optical imaging module 26 is positioned within the primary housing 12 (see FIG. 1B) and underneath the cradles 14. An exemplary optical imaging module 26 includes a long working distance objective 48 at one end, and a sealed CMOS camera 50 at the opposing end. In some embodiments, the camera captures 30 images per second. In some embodiments, the camera captures 40 images per second. In some embodiments, the camera captures 50 images per second. In some embodiments, the camera captures 60 images per second. In some embodiments, the camera captures 70 images per second. In some embodiments, the camera captures more than 70 images per second. This high-speed capturing permits images taken under different conditions or filters to be superimposed. Also shown are tube lenses 52A, 52B and a bandpass filter 54 to enhance imaging. The optical imaging system 26 receives instructions from and sends images to the computer processor 100. Thus, bright field illumination of the well 32 permits the optical imaging system 26 to capture images through the open bottom 34 of the cradle 14 even when the cradle 14 is closed (see FIGS. 2A-2B).

Preferably, the optical imaging system 26 also includes an excitation light source 56, which is shown as a set of LEDs that direct light through a focusing lens 58 or excitation of molecules within the well 32, such as to induce fluorescence for fluorescence imaging. While LEDs correspond to yellow 56A, ultraviolet 56B, and blue 56C are shown, the excitation can include any number between one and seven lights. For example, the excitation light source 56 can include one or more lights including an ultraviolet light, a violet light, a blue light, a green light, a yellow light, an orange light, and a red light. Accordingly, the system 10 is configured to not only capture bright field contrast images of cells but also fluorescent tagged markers, such as fluorescent tagged antibodies, antibody fragments or other molecules that bind to the cell. To this end, the system can providing imaging of different stages of cell proliferation, cell death, cell apoptosis, effector cell killing, cell to cell interaction, cell binding, DNA/RNA/protein upregulation, DNA/RNA/protein down regulation and the like by adding a suitable fluorescent dye or fluorescently tagged molecule to the cell sample and capturing fluorescence by way of the imaging module.

Being part of the optical imaging system 56, the excitation light source 56 is also controlled by the computer processor 100 loaded with software. Thus, the computer processor 100 can instruct the on/off switching of each LED 56A, 56B, 56C and instruct the high speed capture of images via the camera 50. In operation for optical monitoring of the cells, one LED is turned on at a time and the fluorescent image of the corresponding color would be captured by monocolor (black-white) CMOS camera 50. For example, yellow LED 56A, ultraviolet LED 56B, and blue LED 56C would correspond to red, blue and red fluorescent images, respectively. The captured monocolor images would be displayed with pseudo coloring for representation of the corresponding fluorescent color. Moreover, the computer processor 100 can determine the number of live cells from the imaging, as well as determining parameters such as presence or absence of fluorescence (+/−), total fluorescence intensity of the cells in each well or over many wells, average fluorescence intensity for the cells in one well or over more wells, and others. Further, the computer processor 100 can overlay fluorescence image (or single or multiple colors) and bright field illumination image for comprehensive analysis.

Figure 8:
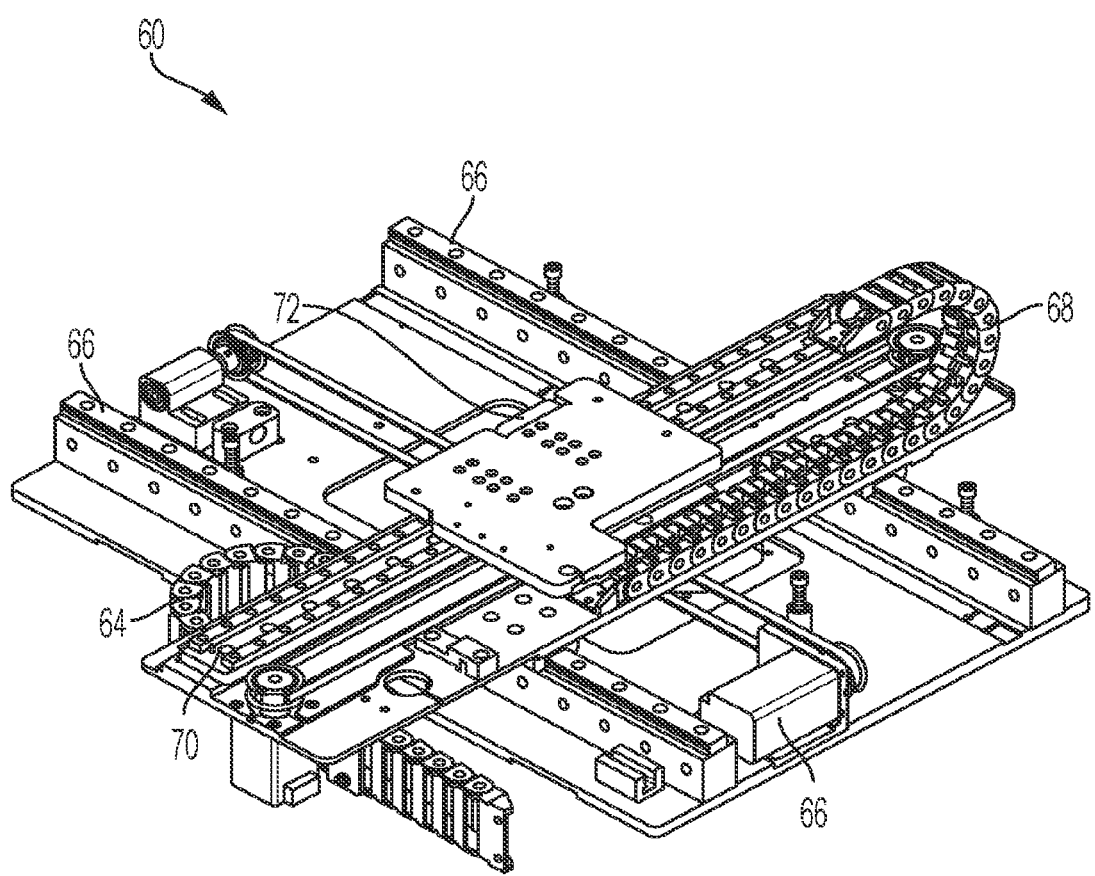
FIG. 8 shows an exemplary optical imaging support 60 for the imaging module 26 of FIG. 6, that allows for two-dimensional linear motions (including motion along an axis parallel to the linear track 66 and along another axis parallel to the linear track 70).

Turning to FIGS. 5, 6 and 8 collectively, the optical module 56 is mounted to a movable support 60 for movement across the different windows 44. Generally only movement along the X and Y axis is needed because lens adjustment or computer controlled focusing can account for minor difference focal lengths between wells 32. As such, the moveable support 60 moves in two directions using an X-axis motor and timing belt 62, an X-axis cable rack 64, an X-axis linear motion guide 66, a Y-axis cable rack 68, and a Y-axis liner motion guide 70. A magnetic linear encoder 72 helps identify the X,Y coordinates of the optical imaging module 56.

As already alluded to, the monitoring system 10 can also store and display data. Data can be displayed on a screen 200, as printed data, or both. Preferably the software can allow entry and display of experimental parameters, such as descriptive information including cell types, compound concentrations, time intervals monitored, etc. Moreover, data can be displayed superimposed, such as combinations showing optical imaging from different fluorescence channels (i.e. different fluorescent colors), bright field illumination and electronic monitoring data.

Preferably, the software can also analyze impedance data. In preferred embodiments, the software can calculate a cell index (CI) for one or more time points for one or more wells. In some preferred embodiments, the software can calculate a cell change index (CCI) from impedance measurements of one or more wells. The software can preferably generate plots of impedance data and impedance values, such as but not limited to CI or CCI, with respect to time. The software may perform other analyses as well, such as calculating cell number from CI, generating dose-response curves based on impedance data, calculating IC values based on impedance values, and calculating kinetic parameters of cell growth or behavior based on impedance values and impedance value curves. The software of the impedance monitoring system can also store and display analyses of the data, such as calculated impedance values and kinetic parameters derived therefrom. Data can be displayed on a screen, as printed data, or both.

Likewise, the software can also be used to analyze captured images. Preferably, the software can perform cell counting functions from images and can plot data over time for statistical analysis. Preferably the software can also store and display analyses of the data, such as counts from fluorescence imaging of different wavelength channels, bright field illumination, and pair superimposed cell imaging results with corresponding electronic monitoring time points.

For example, if the images being captured are bright field images of the cells, the methods of use can include determining cell confluence numbers or parameters from the bright field images or counting cells; or if the images being captured are fluorescence images of the cells, the methods of use can include determining a fluorescence parameter from the images of each color, optionally selected from one or more of the group consisting of total fluorescence counts, total fluorescence intensity, and average fluorescence intensity; or if the images being captured include bright field images of the cells and fluorescence images of the cells, the methods of use can include deriving cell confluence numbers or parameters from the bright field images and optionally counting cells from the bright field images; determining a fluorescence parameter from the fluorescence images, optionally selected from one or more of the group consisting of total fluorescence counts, total fluorescence intensity, and average fluorescence intensity; and optionally, superimposing the bright field images and fluorescence images of one or multiple colors for one or more of the wells.

The benefits of coupling electronic monitoring of cells with live cell imaging are especially evident viewing FIGS. 11A-12C (described in more detail in the below Examples). In particular, whereas cell-substrate impedance was able to detect a rapid staurosporine-mediated effect on A549-Blue cells, the cellular phenomena causing this change could not be deciphered using impedance alone. However, live cell imaging revealed massive cytoplasmic shrinkage, immediately suggesting a mechanistic explanation for the large and rapid impedance response. Likewise, impedance has provided insights that would not have been obtainable by imaging alone. In one such example, MG132 treatment caused cells to detach from electrodes but remain in present in the well (cellular confluence remained >50%, (FIG. 14B), where confluence number is derived from bright field images through image analysis algorithms), while cell imaging showed cells present within the wells, only impedance (the impedance signal dropped to zero (FIG. 11A)) revealed cell-substrate attachment strength. Beyond the benefit of having two independent measurement techniques, it is important to note the objectivity of the impedance readout, which is reported directly, without any processing or input from the user.

Returning to FIGS. 1-8 collectively, non-limited uses of coupling cell-substrate impedance monitoring and live cell imaging of a same cell population are now described in more detail. That is, methods of monitoring cells are disclosed, which include, electronically monitoring cells within wells 32 of a multi-well plate 20, each of the wells 32 having a set of electrodes 42, preferably a set of cell-substrate impedance monitoring electrodes 42, and a transparent window 44 on a bottom surface of the well 32 that is free of electrodes 42; and capturing images through the windows 44 from at least one well 32 that is being or has been electronically monitored. From this monitoring, the methods can include generating an impedance-based curve from the monitored impedance over time (e.g. CI curve); and displaying the impedance-based curve and corresponding optical image(s). Images can be captured from bright field illumination or from fluorescence excitation (e.g. excitation of fluorescent molecule labels attached to antibodies, antibody fragments or other binding molecules). As such, the data can provide quantitative kinetics revealing detailed information regarding cell health, behavior, and cell to cell interactions.

Also disclosed are methods for performing cell proliferation assays. In these assays, an increase in monitored impedance is indicative of an increased cell number, which can be confirmed by corresponding real time imaging. The impedance measurements or impedance values derived from impedance measurements can be plotted versus time to obtain growth curves for cells growing in wells 32 of a multi-well plate 20 and presented with captured cell imaging from the same wells 32, in particular either from bright field illumination and/or from fluorescence imaging of pathways or markers associated with cell proliferation.

Relatedly, methods of generating at least one cell growth curve are provided, which include: incubating cells over time in a multi-well plate 20, where each well 32 includes a set of electrodes 42 and a transparent window 44 on a bottom surface of the well 32 that is free of electrodes 42; monitoring cell-substrate impedance and capturing optical images from a same well 32 through the widow 44; generating an impedance based curve from the monitored impedance; and displaying the impedance based curve and corresponding optical image(s).

Growth curves of one or more cell types coupled with real time cell imaging can be used to determine kinetic parameters. For example, proliferation rates of different primary cancer cells can be compared, or proliferation rates of primary cancer cells of a same type but different grades. In another example, primary cells of individuals of different genotypes can be compared. In another example, proliferation rates of primary or cell line stem cells can be compared. In yet another example, growth curves or parameters of control and genetically modified cells of a cell line can be compared. In yet another example, growth curves or parameters of cells infected with virus and control cells can be compared. Moreover, growth can be confirmed using the imaging features of the system, such as by performing cell counts or cell confluence calculation via images captured through bright field illumination or by counting cells stained with a fluorescent molecule or a fluorescent tagged binding molecule and captured under fluorescence imaging.

The system 10 can also be used to investigate the effect of one or more test compounds on cells. An exemplary embodiment includes incubating cells over time in a multi-well plate 20 where, each well 32 includes a set of electrodes 42 and a transparent window 44 on a bottom surface of the well 32 that is free of electrodes 42; monitoring cell-substrate impedance and capturing optical images from a same well 32 through the window 44; adding a test compound to at least one of the wells 32; continuing to monitor cell-substrate impedance and capturing optical images from the same well 32 through the window 44; generating an impedance based curve from the monitored impedance over time;

and displaying the impedance based curve and optical image(s) from corresponding wells. Changes in effect can be determined by comparing results post compound addition to those prior to compound addition/and or by providing a vehicle control to another well 32 having cells and comparing impedance-based curves and/or images between wells 32.

Also disclosed are methods of comparing the effects of a compound on two or more cell types. An exemplary method includes incubating cells over time in a multi-well plate 20 where, each well 32 includes a set of electrodes 42 and a transparent window 44 on a bottom surface of the well 32 that is free of electrodes 44, where at least one of the wells 32 receives one cell type and at least another well 32 receives a different cell type; monitoring cell-substrate impedance and capturing optical images from each of the wells 32 having cells; adding a same test compound to wells 32 having each of the cell types; continuing to monitor cell-substrate impedance and capturing optical images from each of the wells 32 having cells and test compound through the window 44; generating an impedance based curve from the monitored impedance over time; and displaying impedance based curves and corresponding optical image for each of the wells 32 for comparison with one another. Wells 32 using vehicle controls can also be included as known in the art.

Also disclosed are methods of comparing the effects of two or more different compounds on cells. An exemplary method includes incubating cells over time in a multi-well plate 20 where, each well 32 includes a set of electrodes 42 and a transparent window 44 on a bottom surface of the well 32 that is free of electrodes 42, where at least two of the wells 32 receives cells; monitoring cell-substrate impedance and capturing optical images from each of the wells 32 having cells; adding different test compounds to different wells 32 having cells; continuing to monitor cell-substrate impedance and capturing optical images from each of the wells 32 having cells and test compounds through the windows 44; generating an impedance based curve from the monitored impedances over time; and displaying impedance based curves and corresponding optical image for each of the wells 32 for comparison with one another. Wells 32 using vehicle controls can also be included as known in the art.

Relatedly, also disclosed are methods of performing assays to test the effect of different concentrations of one or more test compound on cells. Such dose response relationships can be used to derive a time-dependent IC5, IC10, IC20, IC30, IC40, IC50, IC60, IC70, IC80, IC90, or IC95, all of which could be derived from a dose response curve. Typically the IC50 is of most interest. Determining a range of time-dependent IC50s for a compound provides information on when the effect of the compound on cells is maximal. Accordingly, an exemplary method includes incubating cells over time in a multi-well plate 20 where, each well 32 includes a set of electrodes 42 and a transparent window 44 on a bottom surface of the well 32 that is free of electrodes 42, where at least two of the wells 32 receives cells; monitoring cell-substrate impedance and capturing optical images from each of the wells 32 having cells; adding different concentrations of a test compound to different wells 32 having cells; continuing to monitor cell-substrate impedance and capturing optical images from each of the wells 32 having cells and test compound through the windows 44; generating impedance based curves from the monitored impedances over time; and displaying impedance based curves and corresponding optical image for each of the wells 32 for comparison with one another, such as to compare their dose response curves or dose relationship or compare IC50 values derived from each of the dose response curves. Wells 32 using vehicle controls can also be included as known in the art.

Also disclosed are methods for performing real-time cytotoxicity assays of a compound. An exemplary embodiment includes incubating cells over time in a multi-well plate 20 where, each well 32 includes a set of electrodes 42 and a transparent window 44 on a bottom surface of the well 32 that is free of electrodes 42; monitoring cell-substrate impedance and capturing optical images from each of the wells 32 having cells; adding a cytotoxic compound or a compound that is suspected of being cytotoxic to one or more wells 32 having cells; continuing to monitor cell-substrate impedance and capturing optical images from each of the wells 32 having cells and the added compound through the windows 44; generating impedance based curve(s) from the monitored impedance(s) over time; and displaying impedance based curve(s) and corresponding optical image(s) for each of the wells 32 for comparison with one another. Wells 32 using vehicle controls can also be included as known in the art.

Also disclosed are methods for analyzing and comparing time-dependent cytotoxic effects of a first compound and a second compound on a cell type. An exemplary embodiment includes incubating cells over time in a multi-well plate 20 where, each well 32 includes a set of electrodes 42 and a transparent window 44 on a bottom surface of the well 32 that is free of electrodes 42; monitoring cell-substrate impedance and capturing optical image(s) from each of the wells 32 having cells; adding a first cytotoxic compound or a first compound that is suspected of being cytotoxic to one or more wells 32 having cells and adding a second cytotoxic compound or a second compound that is suspected of being cytotoxic to another one or more wells 32 having cells; continuing to monitor cell-substrate impedance and capturing optical images from each of the wells 32 having cells and the added compound through the windows 44; generating impedance based curves from the monitored impedances over time; and displaying impedance based curves and corresponding optical images for wells 32 associated with the first and second compound for comparison with one another. Wells 32 using vehicle controls can also be included as known in the art. In some embodiments, time-dependent cytotoxic responses are determined for the first compound at multiple dose concentrations. In some embodiments, time-dependent cytotoxic responses are determined for the second compound at multiple dose concentrations. In some embodiments, time-dependent cytotoxic responses are determined for both first compound and second compound at multiple dose concentrations.

In some embodiment, the first compound is a compound with a known mechanism for its cytotoxic effect and the second compound is a compound with an unknown mechanism for its cytotoxic effect. If the time dependent cytotoxic responses from the second compound are similar to that of the first one, the second compound may follow a similar mechanism for its cytotoxic effect to the first compound.

Various approaches may be used in comparing the cytotoxic responses of the compounds. A cell index (or cell number index) can optionally be calculated using the impedance values obtained. In some embodiments, time dependent IC50 may be derived for the compounds and comparison between their cytotoxic responses is done by comparing their time dependent IC50 curves based on cell index values.

If the IC50 curves follow a similar time-dependent trend, the two compounds may follow a similar mechanism for inducing cytotoxicity effects.

In some embodiments direct comparison of time-dependent cytotoxic responses of two compounds are done where the concentrations for the two compounds may be the same or may be different. Direct comparison between time-dependent cytotoxic responses may be done by analyzing the slope of change in the measured responses (that is equivalent to the first order derivative of the response with respect to time) and comparing the time-dependent slopes for the two compounds. In another approach, the time-dependent cytotoxic responses may be analyzed for their higher order derivatives with respect to time. Comparing such high order derivatives may provide additional information as for the mechanisms of compound-induced cytotoxicity.

In some embodiments analyzing real-time cytotoxicity response may include the derivation of time-dependent IC50 values for the compound on the multiple cell types. In some embodiments, analyzing real-time cytotoxicity response may include derivation of the slope of change in the time dependent cytotoxicity response at a given compound concentration. In some embodiments, analyzing real-time cytotoxicity response may include derivation of high-order derivatives of the time dependent cytotoxicity response with respect to time at a given compound concentration.

Also disclosed are methods for assessing the effect of proposed anticancer therapeutics on cancer cells. An exemplary embodiment includes incubating cancer cells over time in a multi-well plate 20 where, each well 32 includes a set of electrodes 42 and a transparent window 44 on a bottom surface of the well 32 that is free of electrodes; adding one or more proposed therapeutics to the cells; monitoring cell-substrate impedance and capturing optical image(s) from each of the wells 32 having cells; adding effector cells, preferably from a same subject from which the cancer cells were obtained, to the wells 32; continuing to monitor cell-substrate impedance and capturing optical images from each of the wells 32 through the windows 44; generating impedance based curves from the monitored impedances over time; and displaying impedance based curves and corresponding optical images from the wells 32. In some embodiments, the methods include the addition of CAR-T cells as effector cells. Wells 32 using vehicle controls can also be included as known in the art.

Also disclosed are methods for assessing cytolysis of cancer cells by engineered effector cells. An exemplary embodiment includes incubating cancer cells over time in a multi-well plate 20 where, each well 32 includes a set of electrodes 42 and a transparent window 44 on a bottom surface of the well 32 that is free of electrodes 42; monitoring cell-substrate impedance and capturing optical image(s) from each of the wells 32 having cells; adding effector cells engineered to display a binding moiety suspected of binding the cancer cells, preferably from a same subject from which the cancer cells were obtained, to the wells 32; continuing to monitor cell-substrate impedance and capturing optical images from each of the wells 32 through the windows 44; generating impedance based curves from the monitored impedances over time; and displaying impedance based curves and corresponding optical images from the wells 32. Wells 32 using vehicle controls can also be included as known in the art.

Also disclosed are methods for assessing cytolysis of cancer cells by way of a bispecific engager. An exemplary embodiment includes incubating cancer cells over time in a multi-well plate 20 where, each well 32 includes a set of electrodes 42 and a transparent window 44 on a bottom surface of the well 32 that is free of electrodes; monitoring cell-substrate impedance and capturing optical image(s) from each of the wells 32 having cells; adding effector cells to the well 32, preferably from a same patient as the cancer cells; adding a bispecific engager configured to bridge the effector cells to the cancer cells; continuing to monitor cell-substrate impedance and capturing optical images from each of the wells 32 through the windows 44; generating impedance based curves from the monitored impedances over time; and displaying impedance based curves and corresponding optical images from the wells 32. Wells 32 using vehicle controls can also be included as known in the art.

As will be shown in more detail in the Examples that follow, the systems and methods herein couple the simplicity, analytical sensitivity, and objectivity of real-time impedance monitoring with the highly specific readout of live cell imaging to continuously track cellular processes with unparalleled information richness.

Example I

Monitoring of Immune Cell-Mediated Killing of Cancer Target Cells in Real Time

MCF7 breast cancer cells were transfected with a lentivirus expressing a red fluorescent protein (eLenti Red, Cat #8711011), seeded on an E-Plate (ACEA BIOSCIENCES, San Diego, CA) for 25 hours, and then treated with NK92 cells at different effector:target (E:T) ratios.

Figure 9A:
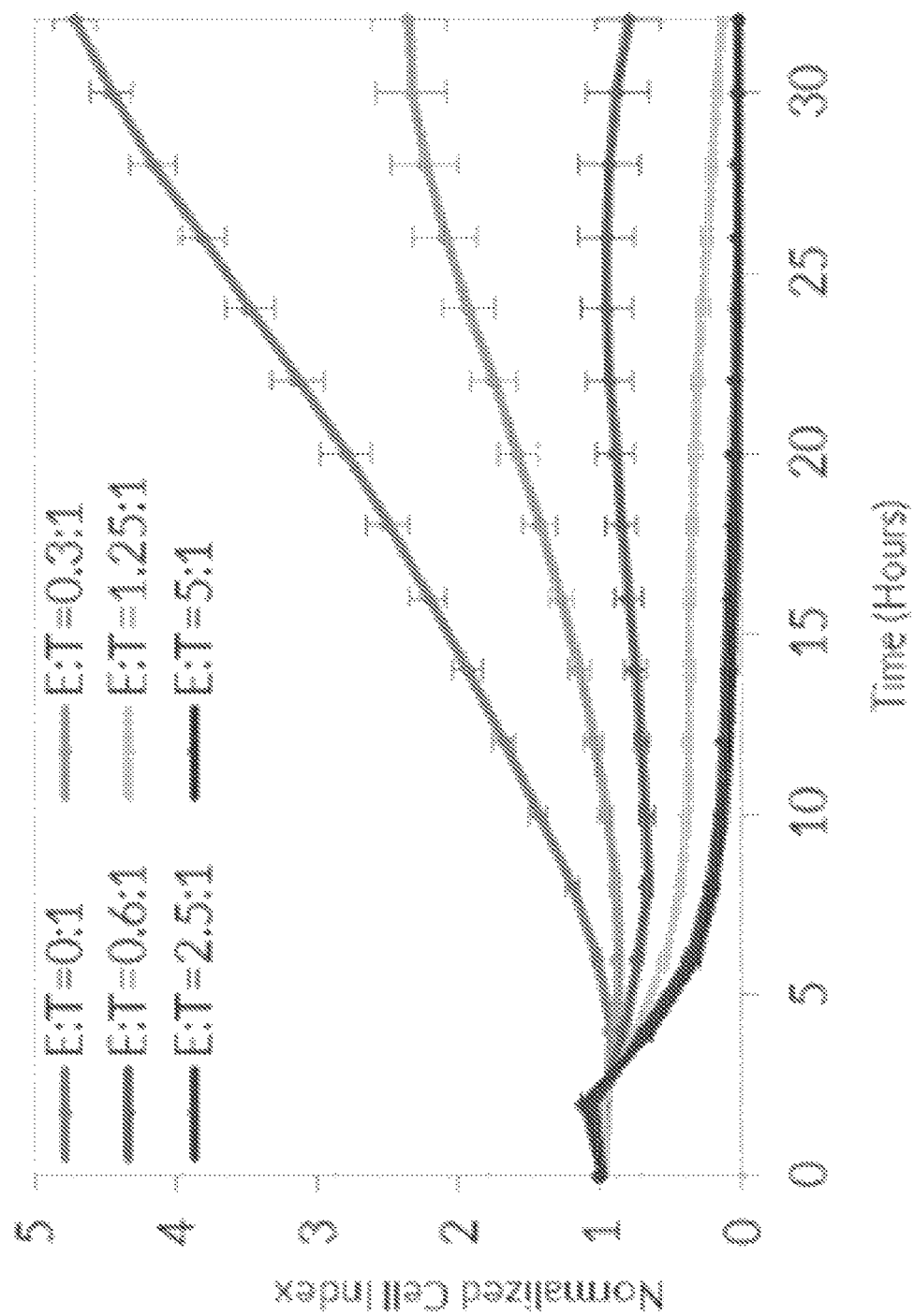
FIG. 9A is an impedance-based graph over a time interval after treating MCF7 breast cancer cells transfected lentivirus expressing a red fluorescent protein, with NK92 cells at different Effector:Target (E:T) ratios over time.
Figure 9B:
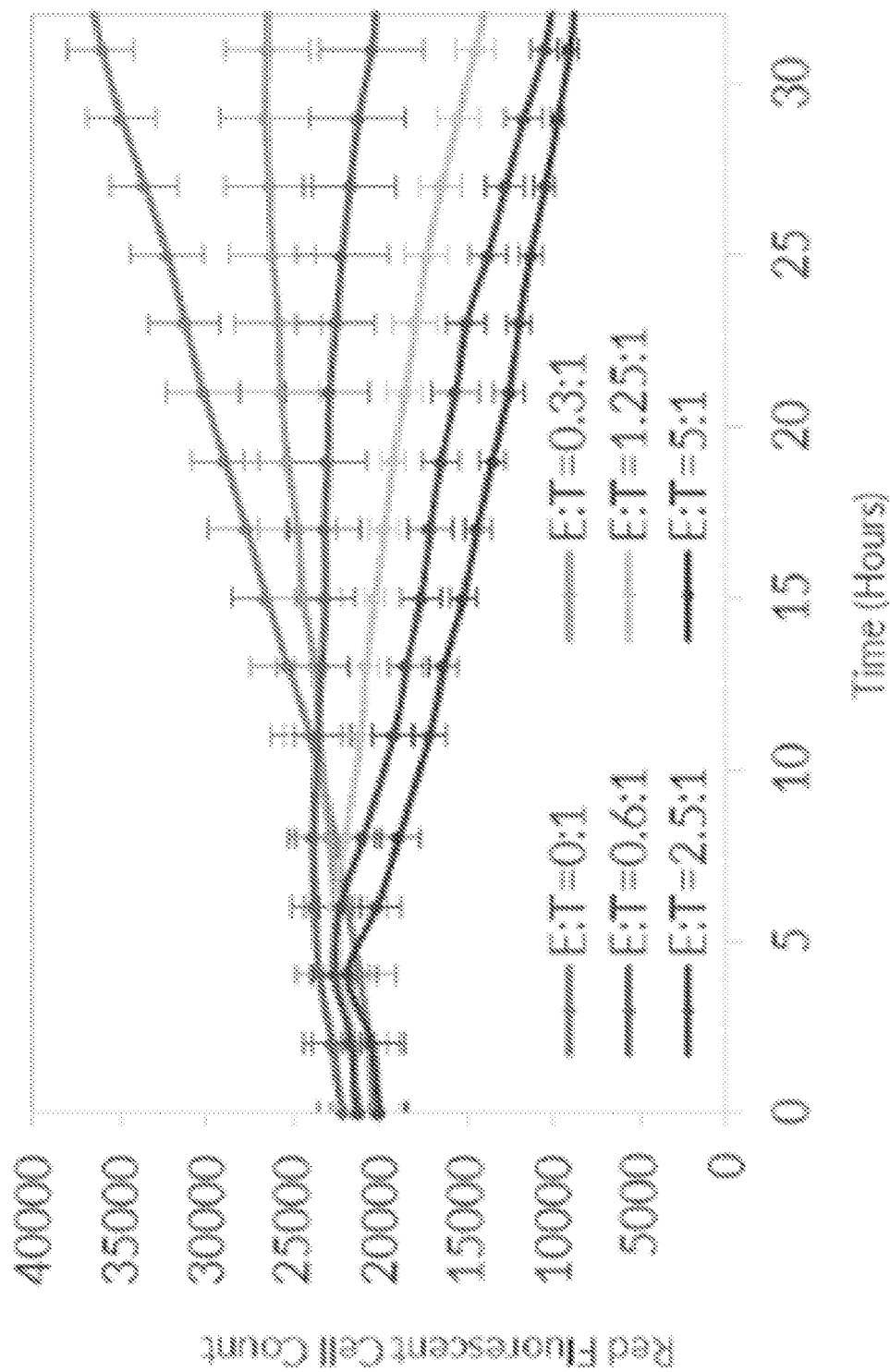
FIG. 9B provides red fluorescent cell count (indicating live target cells) from the same assay over time.

Optical imaging was performed simultaneous with impedance monitoring. As shown in FIGS. 9A-B, effector addition causes cancer cell death in an E:T ratio-dependent manner as demonstrated by impedance monitoring (FIG. 9A) and optical imaging (FIG. 9B). Fluorescent object count (FIG. 9B) indicates number of living target cells.

Figure 9E:
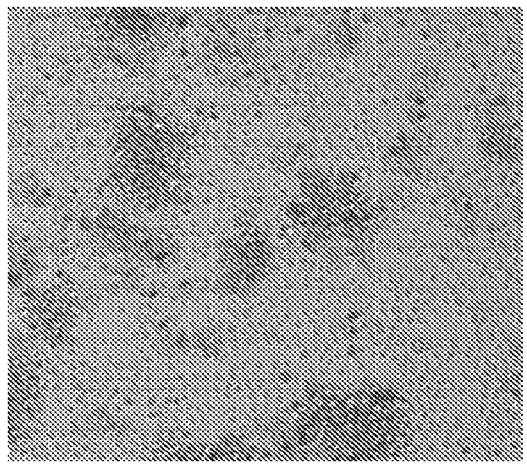
FIGS. 9C-E are images captured under bright field illumination within the same well(s) having an E:T ratio of 2.5:1 before NK92 cell addition (left), 12 hrs. after NK92 cell addition (middle), and 30 hrs after NK92 cell addition.
Figure 9D:
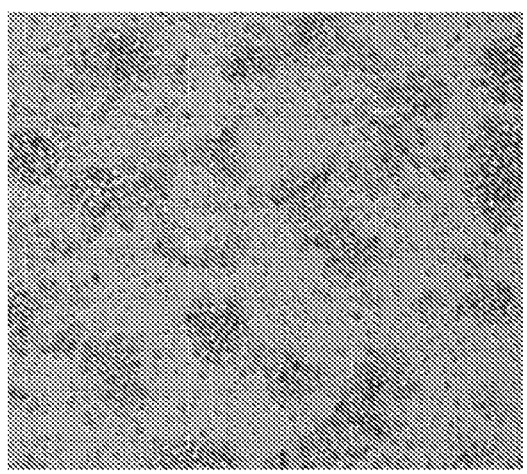
Figure 9C:
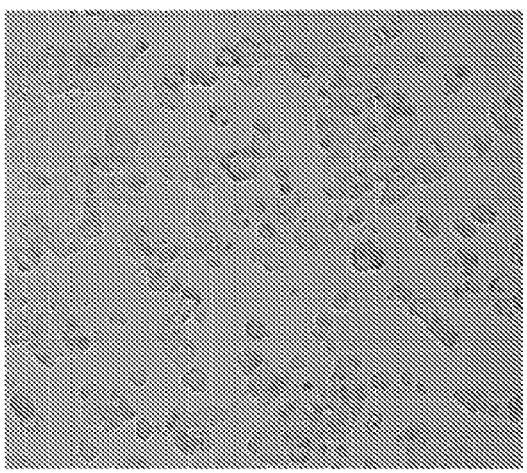
Figure 10:
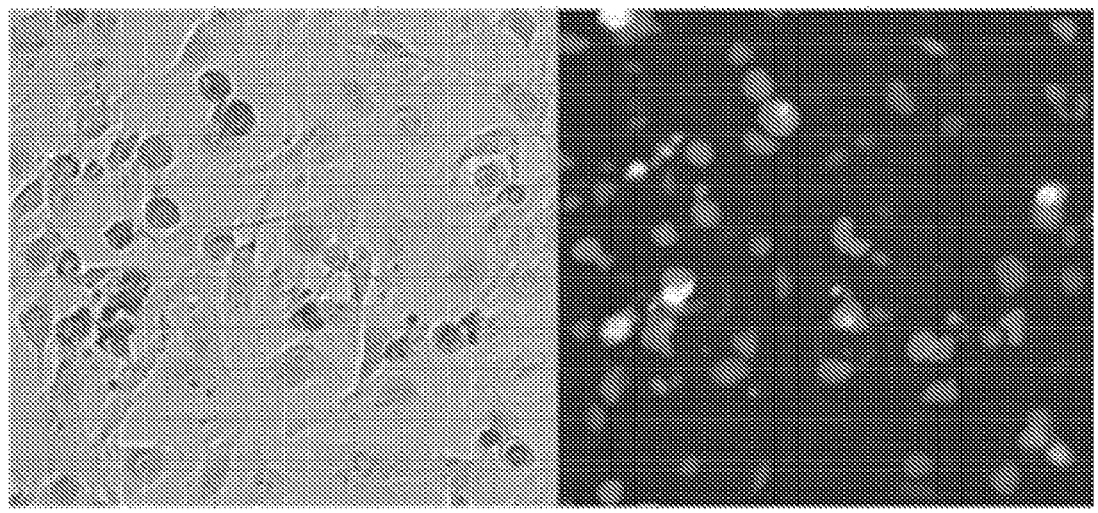
FIG. 10 shows exemplary captured and superimposed images, where the left panel superimposes three captured fluorescent images (red, green and blue) with a captured bright field illumination image, and the right panel superimposes three captured fluorescent images (red, green and blue) without bright field illumination. Shown are cells exposed to fluorescence markers for Annexin V (red), caspase 3 (green), cell nuclei (blue).

FIGS. 9C-9E are images taken before (FIG. 9C), and 30 hr. (FIGS. 9D, 9E) at an E:T ratio of 2.5:1 demonstrating target cell death over time.

Example II

Multiplexing Real-Time Impedance with Live Cell Imaging to Track Cell Killing

Cell maintenance and assays were conducted at 37° C./5% $CO_2$ in F-12K media (ATCC; catalog number 30-2004) containing 10% heat-inactivated FBS (Corning, catalog number 35016CV). While impedance was measured every 15 minutes, images were acquired once per hour. In each well, four fields of view were captured for each channel (brightfield, red, green, and blue). Exposure times were as follows: red (300 ms), green (300 ms), and blue (80 ms). The A549-Blue cell line, which stably expresses nuclear-localized blue fluorescent protein (BFP), was produced by transducing A549 cells (ATCC; catalog number CCL-185) with Agilent eLenti Blue (p/n 8711012) at a multiplicity of infection of 1. From day 2 to day 11 postinfection, 1 µg/mL puromycin was included in the growth medium to select for transductants. For real-time visualization of activated caspase 3, Agilent eCaspase 3 NucView 488 (p/n 8711005) was included in growth medium at a concentration of 5 µm. For real-time visualization of translocated phosphatidylserine, Agilent eAnnexin V Red (p/n 8711007) was included in growth medium at a concentration of 0.25 µg/mL. Agilent E-Plate VIEW microplates (p/n 00300601030) were also used. MG132 (Tocris; catalog number 1748/5) and staurosporine (Calbiochem; catalog number 569396) stocks were dissolved in DMSO.

Figure 11A:
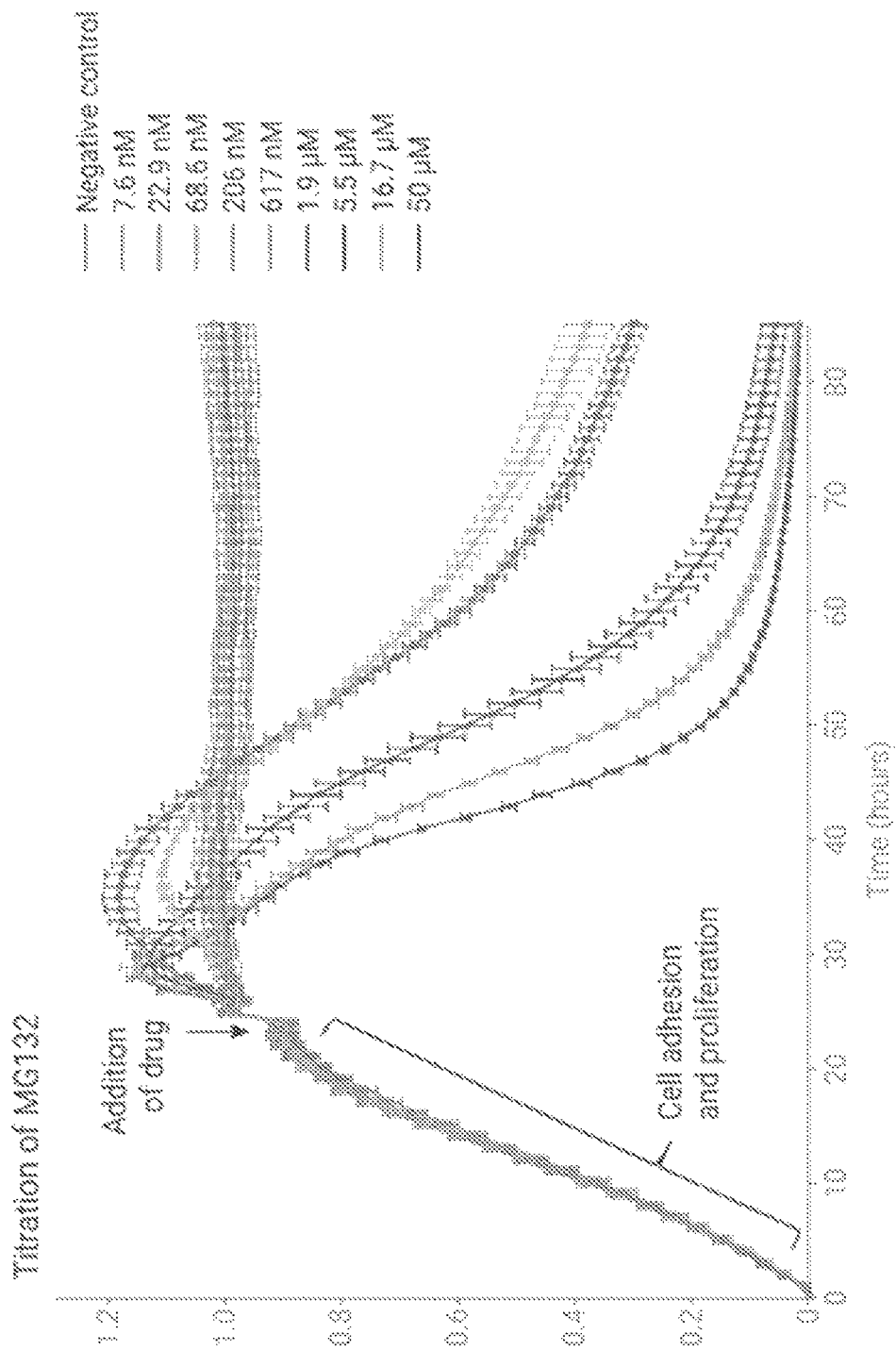
FIGS. 11A-B are graphs depicting cell-substrate impedance monitoring over a time period to demonstrate drug-induced apoptosis in real-time. A549-Blue cells were titrated with either MG132 (FIG. 11A) or staurosporine (FIG. 11B). Negative control was DMSO. Error bars represent the standard deviation from samples run in triplicate. Although impedance was continuously measured at a time interval once every 15 minutes, to prevent the error bars from adjacent time points from overlapping, here data points are only shown once per hour.
Figure 11B:
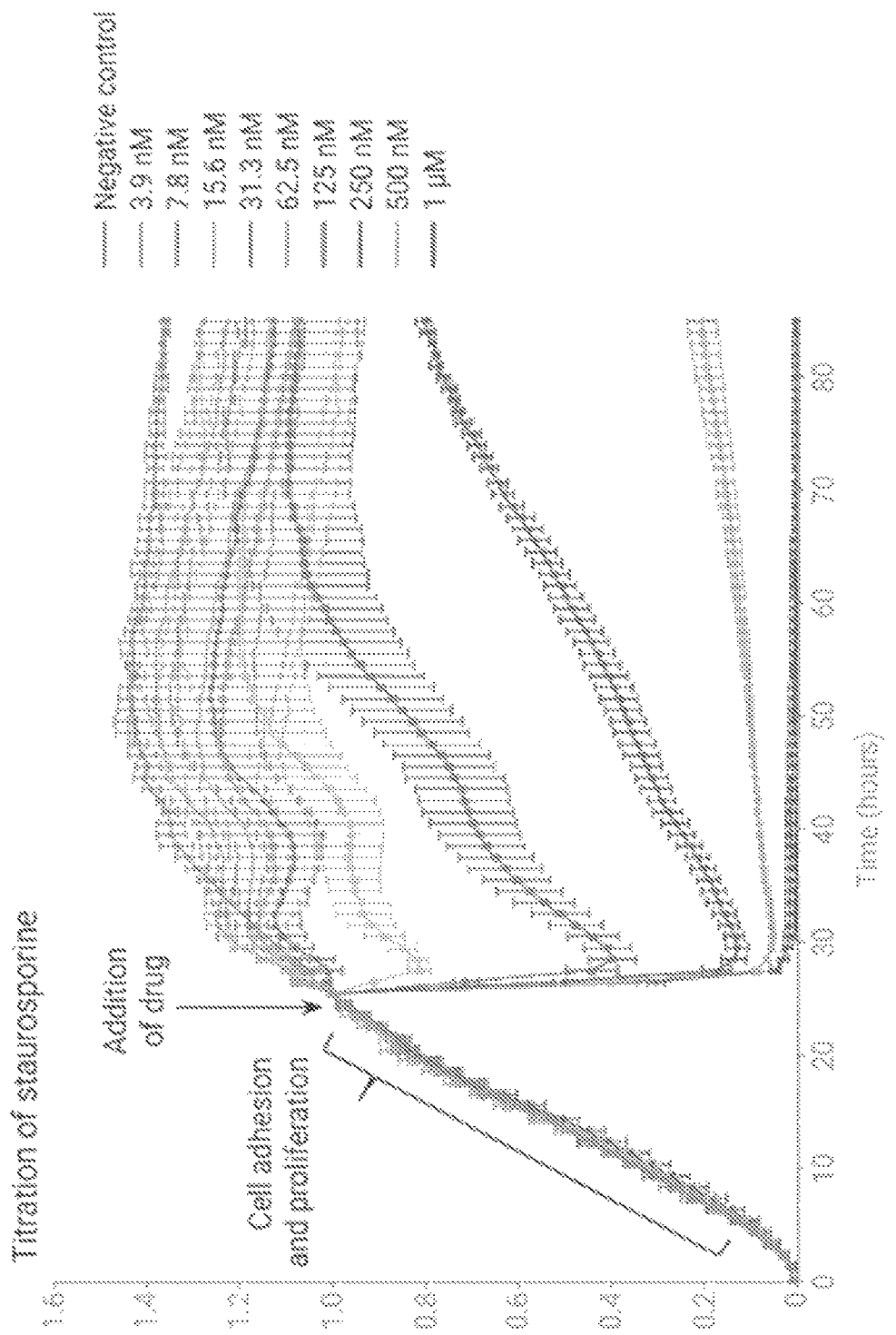

A549-Blue cells (described above) were seeded into an E-PATE VIEW at a density of 10,000 cells/well. As the cells proliferate over the first day, they occupy an expanding surface area on the biosensor array, causing the impedance signal to rise steadily (FIG. 11A and FIG. 11B). If left untreated, the cells grow to confluence, saturating the biosensor array and giving a plateaued impedance signal. Addition of the proteasome inhibitor MG132 or the pan-kinase inhibitor staurosporine at the 25-hour time point induces a marked decrease in the impedance signal in a time- and dose-dependent manner. The kinetics of these drug-induced responses, and the overall shape of the impedance traces, are distinct for each compound. This is consistent with a broad body of literature spanning over 10 years, which has demonstrated that impedance responses are typically unique for each type of mechanism of action. Although MG132 and staurosporine both induce apoptosis, they elicit distinct cellular behaviors en route to cell death, which becomes strikingly clear when real-time impedance is multiplexed with live cell imaging.

Figure 12A:
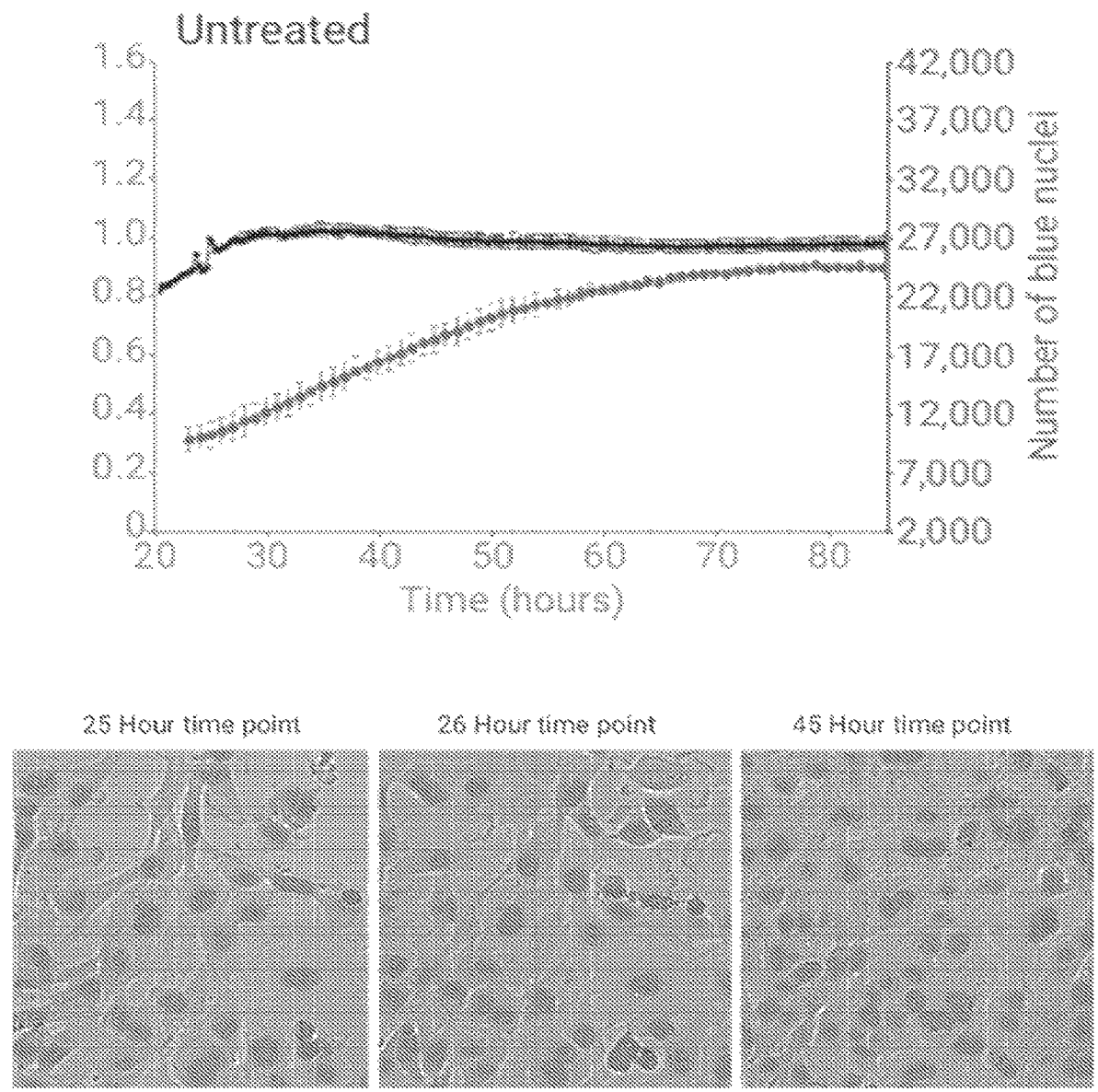
FIGS. 12A-C provide a graph plotting impedance monitoring over a time period in combination with live cell imaging at different time points within the impedance monitoring time period. The impedance signal and the number of blue nuclei were tracked after treating A549-Blue cells with either DMSO (FIG. 12A), 50 μm MG132 (FIG. 12B), or 1 μm staurosporine (FIG. 12C). Representative images are shown for pretreatment and 1 or 20 hours after treatment. Error bars represent the standard deviation from samples run in triplicate.

Although A549-Blue cells already cover most of the well bottom by the 26-hour time point, in the absence of drug, they continue proliferating for another 50 hours, packing cells together at higher density (FIG. 12A). Consistent with this, the impedance signal plateaus at roughly 30 hours while the total number of blue nuclei continues to increase until ~80 hours (FIG. 12A). Blue nuclei count is Obtained by an image processing algorithm to count the number of blue objects in the blue-fluorescent image. Each blue nuclei nucleus corresponds to an A549 cell as it was transduced to expresses nuclear-localized blue fluorescent protein. As such the number of blue nuclei in a well correspond to the number of viable A549-blue cells present in the well. When A549-Blue cells are treated with the four highest concentrations of MG132 (1.9, 5.5, 16.7, and 50 μm), the total number of blue nuclei decreases over time in a manner that correlates well with the drop in impedance (FIG. 12B; only data for the 50 μm treatment are shown). In contrast, treating the cells with the four highest concentrations of staurosporine (0.125, 0.250, 0.500, and 1 μm) causes impedance to plummet within the first few minutes, but has a modest impact on the number of blue nuclei over the subsequent 60 hours (FIG. 12C; only data for the 1 μm treatment are shown). Consistent with its ability to cause cells to expel water, one hour after staurosporine addition, the A549-Blue cells have shrunk so severely that their cytoplasm is barely visible and only blue nuclei remain. Although, over time, these nuclei shrink in size and begin clustering together, they largely remain intact, explaining why the number of blue nuclei stays fairly constant in FIG. 12C. The above coupling of impedance with imaging clearly provides a more complete and nuanced understanding of drug-mediated A549 cell killing than would be possible using either technique alone. Moving beyond simple cell counts, we next probed the kinetics of biochemical phenomena that are specific to the apoptotic killing pathway.

Example III

Simultaneous Tracking MG132-Mediated Apoptosis from Five Different Perspectives

Figure 13:
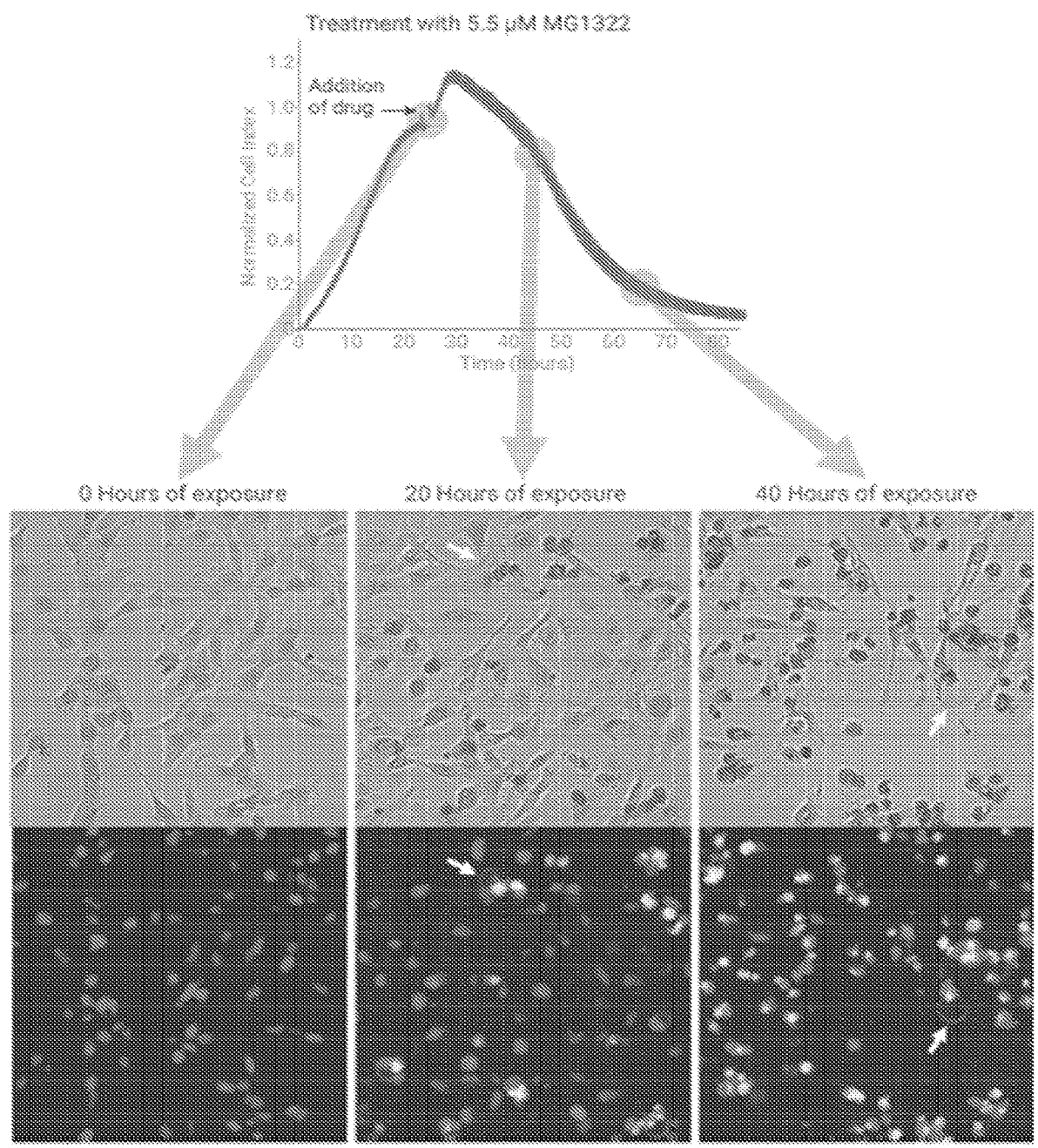
FIG. 13 provides an impedance-based plot before and after treatment with 5.5 μM MG1322. Also shown are images taken 0 hour after treatment, 20 hours after treatment, and 40 hours after treatment. Top images are each taken under bright field illumination and the bottom images are taken under fluorescence, with Annexin V staining (red), activated caspase 3 (green), and nuclear-localized BFP (blue fluorescent protein). Arrows denote large membrane blebs that contain phosphatidylserine in their outer leaflet.

Along with impedance and blue nuclei counts, the induction of apoptosis by MG132 was also tracked by percent cellular confluence, caspase 3 activation (causing cells to fluoresce green), and phosphatidylserine translocation (causing cells to fluoresce red). As seen in FIG. 13, the drug-induced drop in impedance correlates well with the temporal accumulation of these apoptosis-specific markers. The bold white arrows in the panels for the 20- and 40-hour time points highlight large membrane blebs that contain phosphatidylserine in their outer leaflet.

Figure 12B:
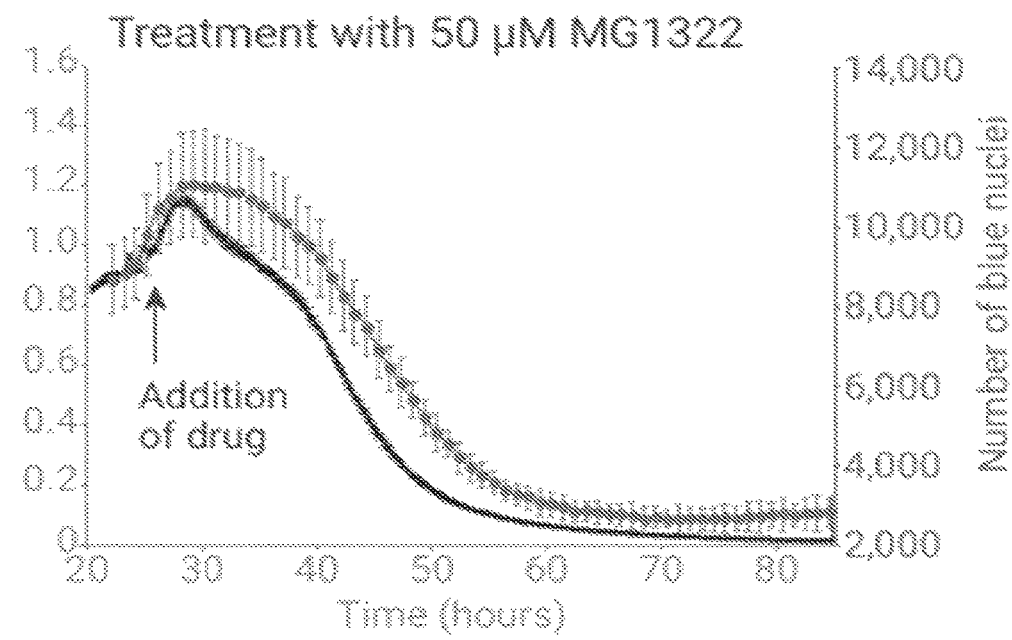
Figure 12B:
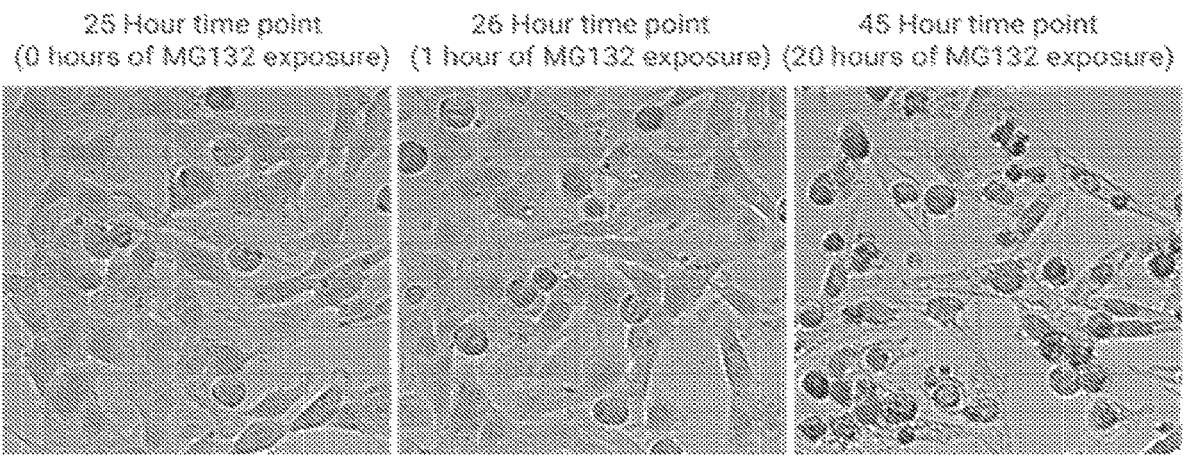
Figure 12C:
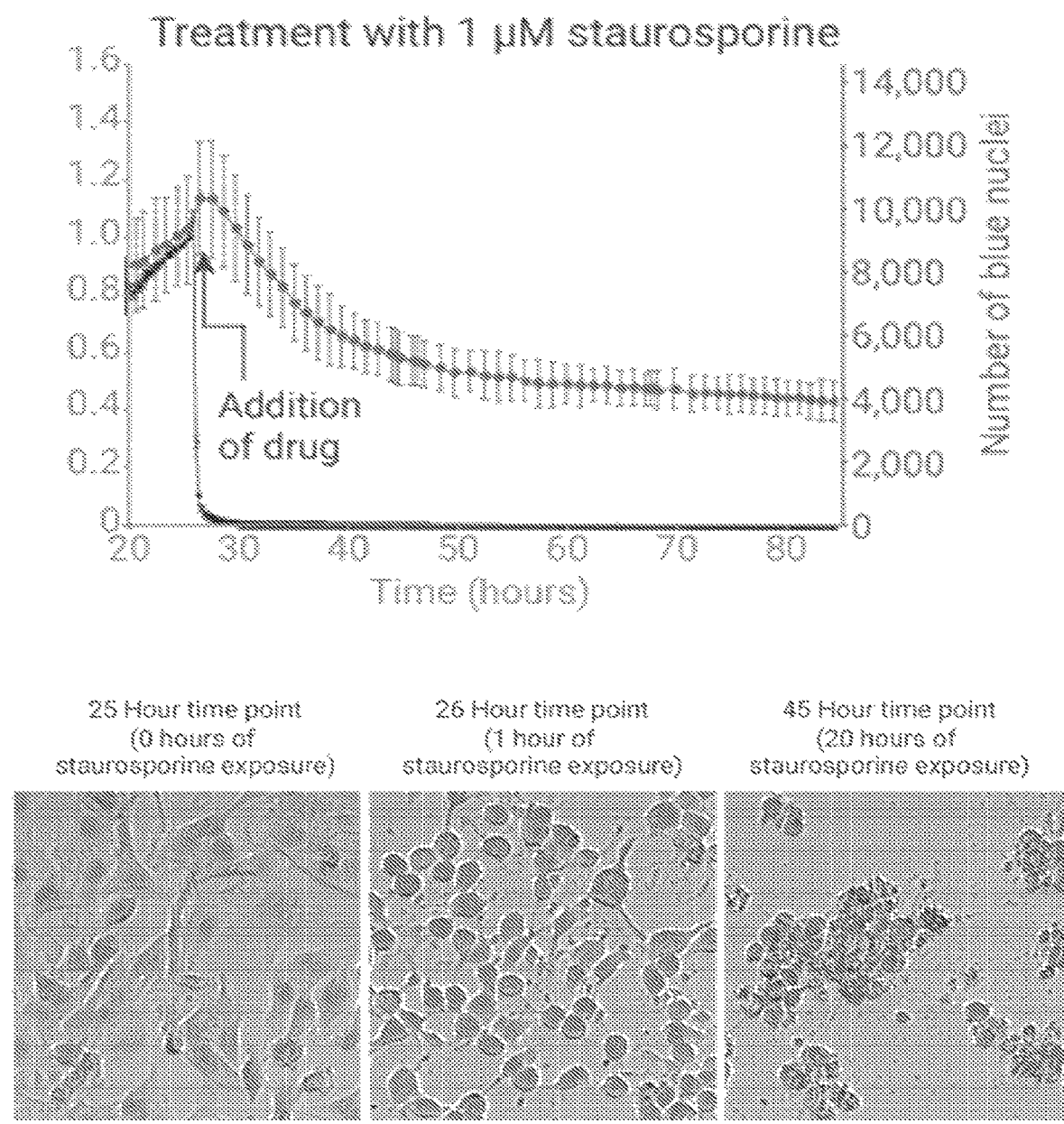
Figure 14A:
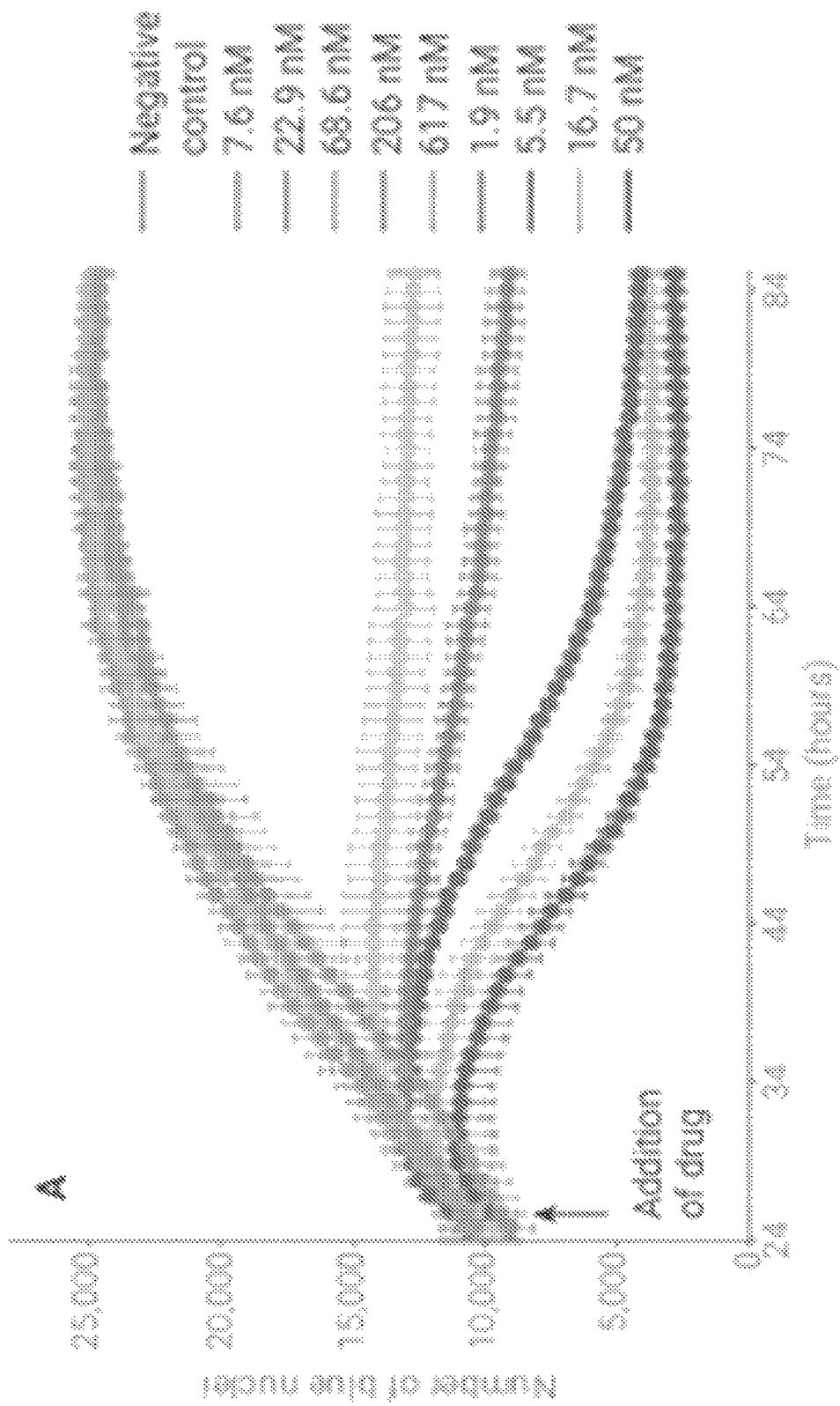
FIGS. 14A-D provide graphs showing image-based continuous tracking MG132-induced apoptosis in A549-Blue cells using number of blue nuclei (FIG. 14A), % confluence (FIG. 14B), number of green (caspase 3 activated) cells (FIG. 14C), and number of red (annexin V-bound) cells (FIG. 14D). Error bars represent the standard deviation from samples run in triplicate.
Figure 14B:
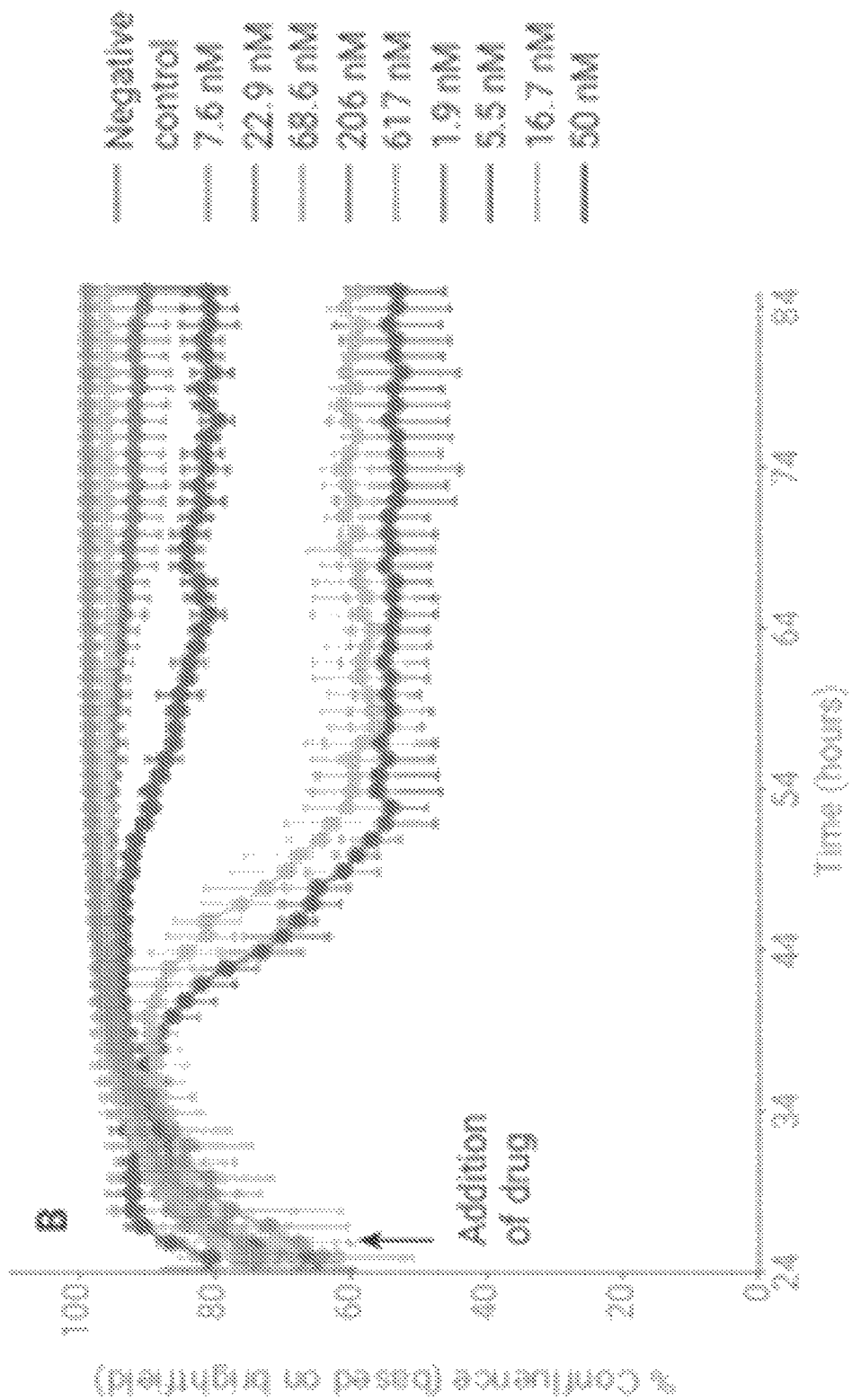
Figure 14C:
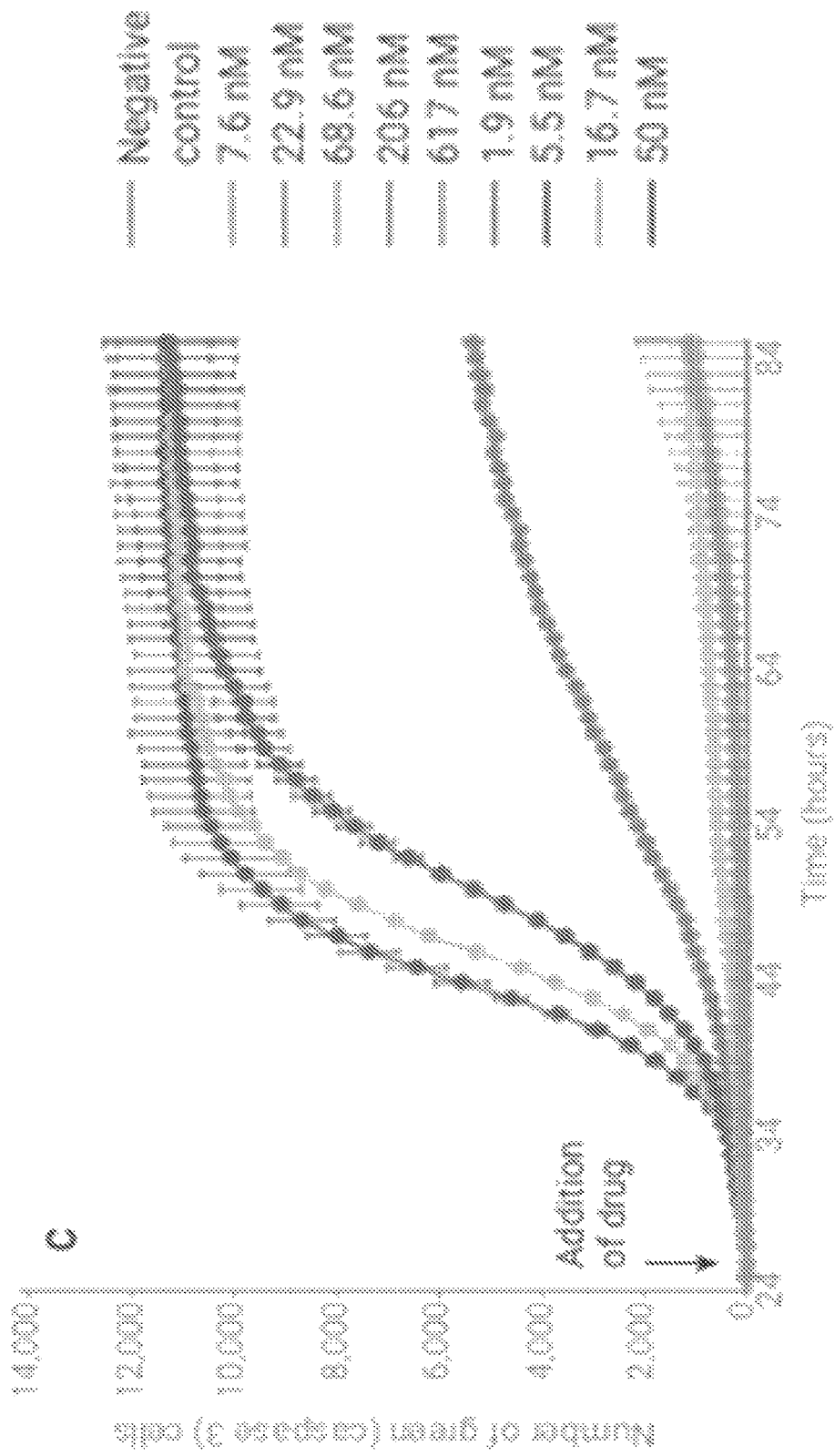
Figure 14D:
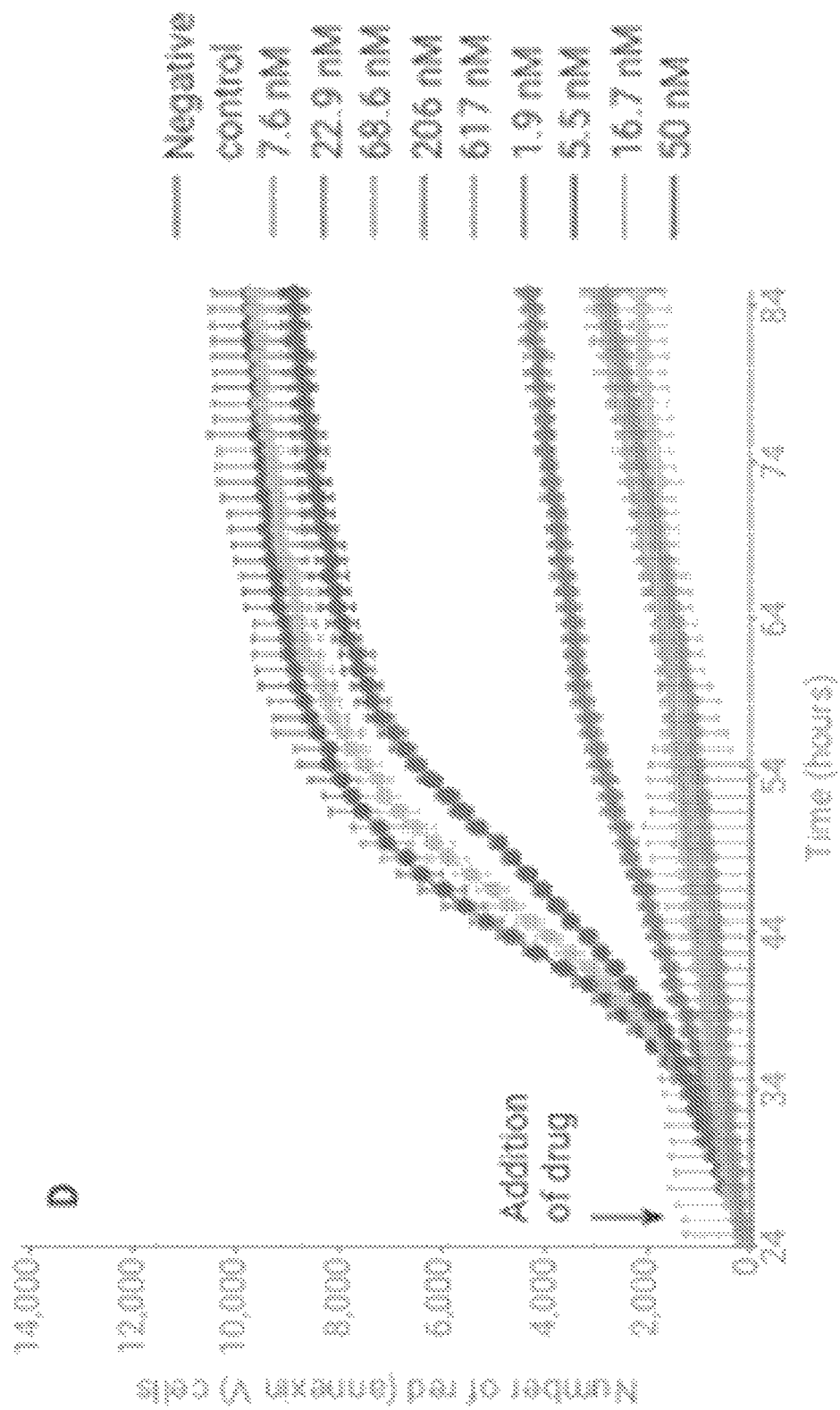
Figure 15:
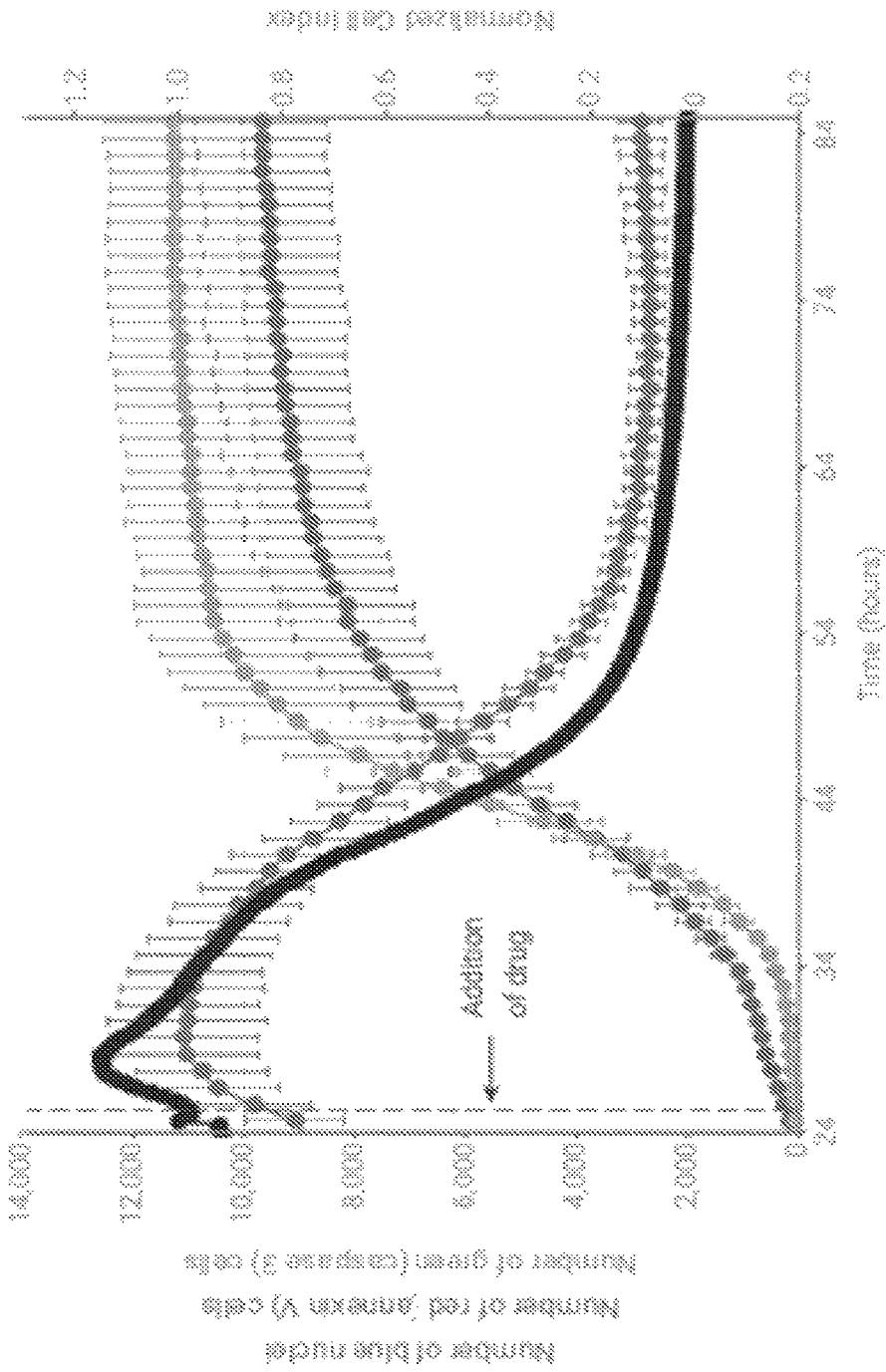
FIG. 15 is a graph showing comparing the relative rate and relative abundance of different apoptotic phenomena for cells treated with 50 μM MG132. Error bars represent the standard deviation from samples run in triplicate.

Next, the continuous response of A549-Blue cells to MG132 was plotted using each of the image-based readouts. Blue nuclei counts (FIG. 14A) (FIG. 14A) display a dependency on drug concentration that closely reflects the impedance responses seen in (FIG. 11A), Despite the extensive apoptotic response, throughout the course of this assay the % cellular confluence never drops below 50% (FIG. 14B), where the cell confluence number is derived from bright field images through image processing algorithms. This is consistent with the fact that, unlike in vivo contexts, where apoptotic cells and their debris are removed through phagocytosis, in vitro, a large percentage of apoptotic cells continue to occupy the well bottom (FIG. 12B). The fact that high concentrations of MG132 cause the impedance signal to drop to zero (FIG. 11A) while the % confluence never drops below 50% indicates that residual cells are no longer attached to the plate bottom. The number of caspase 3 positive (fluorescence green) objects (FIG. 14C) and the number of the annexin V positive (fluorescent red) objects (FIG. 14D) increase over time, and display clear dependencies on MG132 concentration. Considering the number of cells that were seeded, their rate of growth, and the percentage of cells that display apoptotic markers (FIG. 13), the output numbers in FIGS. 14A-C are consistent with expectations. To compare the relative rates and relative abundance of different apoptotic phenomena, the impedance response was plotted alongside three different image-based readouts (FIG. 15). As expected, the time at which the number of blue nuclei begins to decrease (~10 hours after MG-132 addition) is the same time that caspase 3 activation and phosphatidylserine translocation become detectable. For the first 20 hours of drug treatment, the number of cells displaying caspase 3 and phosphatidylserine signals is similar, but over the subsequent 40 hours, the number of caspase 3-activated cells exceeds the number of phosphatidylserine translocated cells by approximately 20%.

Example IV

Figure 16:
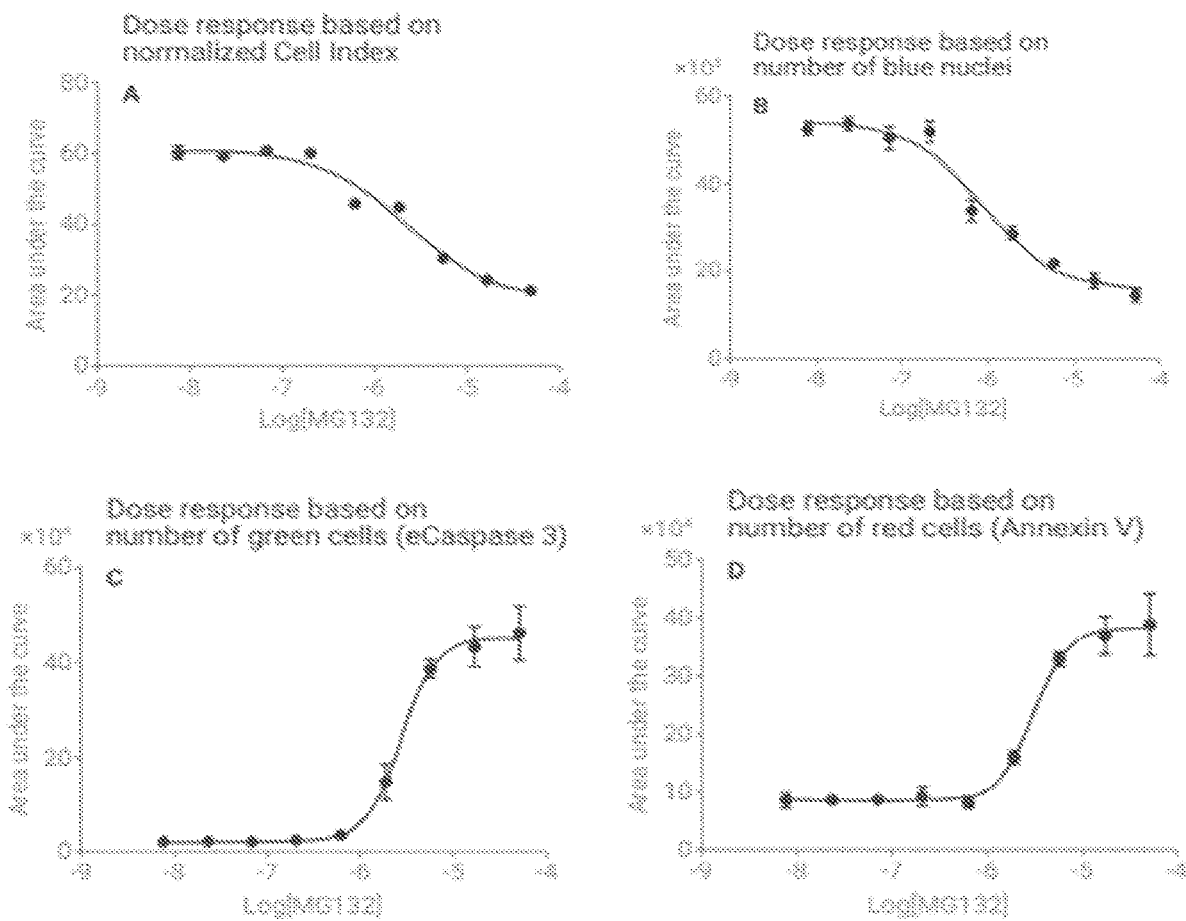
FIG. 16 provides a table and graphs showing the use of dose response curves to calculate EC50. Using real-time impedance (as represented by normalized cell index) data (FIG. 11A) and live cell imaging (green cell number, red cell number and blue nuclei number) data (FIGS. 14A-C), area under the curve was calculated, and is plotted here as a function of MG132 concentration. Data were fit to a four-parameter logistic equation to determine the EC50.

Quantifying Drug Efficacy by Simultaneous Monitoring of Cell-Substrate Impedance and Optical Imaging Using the impedance and image-based readouts presented in Examples II-IV, the EC50 for MG132 was calculated. The area under the curve, spanning from the time of drug addition to 60 hours after drug addition, was plotted as a function of MG132 concentration to yield the dose response curves seen in FIG. 16. The quality of the fitting for the four different readouts is quite good, with R2 values ranging from 0.96 to 0.98. The calculated EC50 values range from 0.86 to 3.0 μm, which is consistent with values reported in the literature. See Han, Y. H. et al. The Effect of MG132, a Proteasome Inhibitor on HeLa Cells in Relation to Cell Growth, Reactive Oxygen Species and GSH. *Oncol. Rep.* 2009, 22(1), 215-21.

What is claimed is:
1. A system for electronically and optically monitoring biological samples, the system comprising:

a multi-well plate having a plurality of wells configured to receive a plurality of biological samples comprising cells, each well of the plurality of wells comprising a set of monitoring electrodes and a transparent window on a bottom surface thereof that is free of electrodes;

an optical imaging module configured to be disposed adjacent to the plurality of wells of the multi-well plate to capture images of biological samples of the plurality of biological samples via light passing through the transparent window of a corresponding well of the plurality of wells;

a computer processor communicatively coupled to a corresponding set of monitoring electrodes for each well of the plurality of wells and the optical imaging module; and an illumination module having one or more light sources coupled to the computer processor for selectively illuminating one or more wells of the plurality of wells;

wherein the computer processor is programmed to operate one or more of the multi-well plate and optical imaging module according to the following operations:

controlling operation of the corresponding set of monitoring electrodes for each well of the plurality of wells in the multi-well plate to electrically monitor the plurality of biological samples or analyzing electrically monitored data acquired therefrom in response to image data received from the optical imaging module;

selectively illuminating the one or more light sources in response to acquired changes in cell-substrate impedance monitoring for cell imaging to identify a change in a population of cells within the plurality of wells; and operating the optical imaging module to capture image data of one or more of the plurality of biological samples across the plurality of wells or analyzing image data acquired therefrom in response to the electrically monitored data acquired by the corresponding set of monitoring electrodes for each well of the plurality of wells.

2. The system of claim 1, wherein the optical imaging module is movable across different wells of the multi-well plate.

3. The system of claim 2, further comprising:

a cradle configured to receive the multi-well plate, the cradle having an opening on a bottom surface of the cradle to expose each transparent window of the plurality of wells;

wherein the computer processor is communicatively coupled to the cradle and programmed to:

selectively operate each set of monitoring electrodes for electronically monitoring cell-substrate impedance within one or more wells of the plurality of wells;

operate the illumination module for selectively illuminating the one or more wells of the plurality of wells; and operate the optical imaging module to selectively move the optical imaging module relative to the multi-well plate and capture the image data from the one or more wells of the plurality of wells.

4. The system of claim 1, wherein the illumination module is positioned above the one or more wells of the plurality of wells.

5. The system of claim 1, wherein the computer processor is further programmed to:

operate the optical imaging module to initiate capturing of the image data from one or more wells of the plurality of wells in response to the one or more wells reaching or following a set impedance-based value or impedance-based parameter from electronic monitoring of the plurality of biological samples via the corresponding set of monitoring electrodes for each well of the plurality of wells.

6. The system of claim 5, wherein the set impedance-based value or impedance-based parameter is indicative of an established cell monolayer or established cell population.

7. The system of claim 1, wherein the computer processor is further programmed to:

operate the set of monitoring electrodes and communicate with impedance measurement circuitry to initiate electronic monitoring of the cells via the set of monitoring electrodes as a function of the image data.

8. The system of claim 7, wherein the computer processor is further programmed to:

perform one or more of cell counting and cell confluence analysis on the image data to identify whether cells are properly settled against the bottom surface of a given well of the plurality of wells prior to initiating the corresponding set of monitoring electrodes to conduct electronic monitoring.

9. The system of claim 1, wherein the computer processor is further programmed to input the image data to analyze one or more characteristics of the electronically monitored data.

10. The system of claim 9, wherein the computer processor is further programmed to identify via the image data a mechanism contributing to the one or more characteristics of the electronically monitored data, the mechanism not being readily identifiable by analyzing the electronically monitored data alone.

11. The system of claim 1, wherein the computer processor is further programmed to use the electronically monitored data from to analyze one or more characteristics of the image data.

12. The system of claim 11, wherein the computer processor is further programmed to use the electronically monitored data to identify a mechanism contributing to the one or more characteristics of the image data, the mechanism not being readily identifiable by analyzing the acquired image data alone.

13. The system of claim 1, wherein the optical imaging module further comprises an excitation light source configured to excite one or more molecules in the biological samples.

14. The system of claim 13, wherein the excitation light source comprises one or more lights selected from the group consisting of an ultraviolet light, a violet light, a blue light, a green light, a yellow light, an orange light, and a red light.

15. The system of claim 1, wherein the wells are sequentially imaged via motion of the optical imaging module.

16. The system of claim 15, wherein the wells are sequentially imaged a single well at a time, and a moved via a motors of a movable support along a first axis and a second axis that are controlled by the computer processor to move at predefined time intervals.

17. A system for electronically and optically monitoring biological samples, the system comprising:

a multi-well plate having a plurality of wells configured to receive a plurality of biological samples comprising cells, each well of the plurality of wells comprising a set of monitoring electrodes and a transparent window on a bottom surface thereof that is free of electrodes;

an optical imaging module configured to be disposed adjacent to the plurality of wells of the multi-well plate to capture images of biological samples of the plurality of biological samples via light passing through the transparent window of a corresponding well of the plurality of wells;

a computer processor communicatively coupled to a corresponding set of monitoring electrodes for each well of the plurality of wells and the optical imaging module; and an illumination module having one or more light sources coupled to the computer processor for selectively illuminating one or more wells of the plurality of wells;

wherein the computer processor is programmed to operate one or more of the multi-well plate and optical imaging module according to the following operations:

controlling operation of the corresponding set of monitoring electrodes for each well of the plurality of wells in the multi-well plate to electrically monitor the plurality of biological samples or analyzing electrically monitored data acquired therefrom in response to image data received from the optical imaging module;

operating the optical imaging module to initiate capturing of the image data from one or more wells of the plurality of wells in response to the one or more wells reaching or following a set impedance-based value or impedance-based parameter from electronic monitoring of the plurality of biological samples via the corresponding set of monitoring electrodes for each well of the plurality of wells; and operating the optical imaging module to capture image data of one or more of the plurality of biological samples across the plurality of wells or analyzing image data acquired therefrom in response to the electrically monitored data acquired by the corresponding set of monitoring electrodes for each well of the plurality of wells.

18. The system of claim 17, wherein the computer processor is further programmed to selectively illuminate the one or more light sources in response to acquired changes in cell-substrate impedance monitoring for cell imaging to identify a change in a population of cells within the plurality of wells.

19. The system of claim 17, wherein the optical imaging module is movable across different wells of the multi-well plate.

20. The system of claim 19, further comprising:
a cradle configured to receive the multi-well plate, the cradle having an opening on a bottom surface of the cradle to expose each transparent window of the plurality of wells;
wherein the computer processor is communicatively coupled to the cradle and programmed to:
selectively operate each set of monitoring electrodes for electronically monitoring cell-substrate impedance within one or more wells of the plurality of wells;
operate the illumination module for selectively illuminating the one or more wells of the plurality of wells; and
operate the optical imaging module to selectively move the optical imaging module relative to the multi-well plate and capture the image data from the one or more wells of the plurality of wells.

21. The system of claim 17, wherein the illumination module is positioned above the one or more wells of the plurality of wells.

22. The system of claim 17, wherein the set impedance-based value or impedance-based parameter is indicative of an established cell monolayer or established cell population.

23. The system of claim 17, wherein the computer processor is further programmed to:
operate the set of monitoring electrodes and communicate with impedance measurement circuitry to initiate electronic monitoring of the cells via the set of monitoring electrodes as a function of the image data.

24. The system of claim 23, wherein the computer processor is further programmed to:
perform one or more of cell counting and cell confluence analysis on the image data to identify whether cells are properly settled against the bottom surface of a given well of the plurality of wells prior to initiating the corresponding set of monitoring electrodes to conduct electronic monitoring.

25. The system of claim 17, wherein the computer processor is further programmed to input the image data to analyze one or more characteristics of the electronically monitored data.

26. The system of claim 25, wherein the computer processor is further programmed to identify via the image data a mechanism contributing to the one or more characteristics of the electronically monitored data, the mechanism not being readily identifiable by analyzing the electronically monitored data alone.

27. The system of claim 17, wherein the computer processor is further programmed to use the electronically monitored data to analyze one or more characteristics of the image data.

28. The system of claim 17, wherein the computer processor is further programmed to use the electronically monitored data to identify a mechanism contributing to the one or more characteristics of the image data, the mechanism not being readily identifiable by analyzing the acquired image data alone.

29. The system of claim 17, wherein the optical imaging module further comprises an excitation light source configured to excite one or more molecules in the biological samples.

30. The system of claim 29, wherein the excitation light source comprises one or more lights selected from the group consisting of an ultraviolet light, a violet light, a blue light, a green light, a yellow light, an orange light, and a red light.

31. The system of claim 17, wherein the wells are sequentially imaged via motion of the optical imaging module.

32. A system for electronically and optically monitoring biological samples, the system comprising:
a multi-well plate having a plurality of wells configured to receive a plurality of biological samples comprising cells, each well of the plurality of wells comprising a set of monitoring electrodes and a transparent window on a bottom surface thereof that is free of electrodes;
an optical imaging module configured to be disposed adjacent to the plurality of wells of the multi-well plate to capture images of biological samples of the plurality of biological samples via light passing through the transparent window of a corresponding well of the plurality of wells;
a computer processor communicatively coupled to a corresponding set of monitoring electrodes for each well of the plurality of wells and the optical imaging module; and
an illumination module having one or more light sources coupled to the computer processor for selectively illuminating one or more wells of the plurality of wells;
wherein the computer processor is programmed to operate one or more of the multi-well plate and optical imaging module according to the following operations:
controlling operation of the corresponding set of monitoring electrodes for each well of the plurality of wells in the multi-well plate to electrically monitor the plurality of biological samples or analyzing electrically monitored data acquired therefrom in response to image data received from the optical imaging module;

operating the optical imaging module to capture image data of one or more of the plurality of biological samples across the plurality of wells or analyzing image data acquired therefrom in response to the electrically monitored data acquired by the corresponding set of monitoring electrodes for each well of the plurality of wells; and operating the set of monitoring electrodes and communicate with impedance measurement circuitry to initiate electronic monitoring of the cells via the set of monitoring electrodes as a function of the image data.

33. The system of claim 32, wherein the computer processor is further programmed to selectively illuminate the one or more light sources in response to acquired changes in cell-substrate impedance monitoring for cell imaging to identify a change in a population of cells within the plurality of wells.

34. The system of claim 32, wherein the optical imaging module is movable across different wells of the multi-well plate.

35. The system of claim 34, further comprising:

a cradle configured to receive the multi-well plate, the cradle having an opening on a bottom surface of the cradle to expose each transparent window of the plurality of wells;

wherein the computer processor is communicatively coupled to the cradle and programmed to:

selectively operate each set of monitoring electrodes for electronically monitoring cell-substrate impedance within one or more wells of the plurality of wells;

operate the illumination module for selectively illuminating the one or more wells of the plurality of wells; and operate the optical imaging module to selectively move the optical imaging module relative to the multi-well plate and capture the image data from the one or more wells of the plurality of wells.

36. The system of claim 32, wherein the illumination module is positioned above the one or more wells of the plurality of wells.

37. The system of claim 32, wherein the computer processor is further programmed to:

operate the optical imaging module to initiate capturing of the image data from one or more wells of the plurality of wells in response to the one or more wells reaching or following a set impedance-based value or impedance-based parameter from electronic monitoring of the plurality of biological samples via the corresponding set of monitoring electrodes for each well of the plurality of wells.

38. The system of claim 37, wherein the set impedance-based value or impedance-based parameter is indicative of an established cell monolayer or established cell population.

39. The system of claim 32, wherein the computer processor is further programmed to:

perform one or more of cell counting and cell confluence analysis on the image data to identify whether cells are properly settled against the bottom surface of a given well of the plurality of wells prior to initiating the corresponding set of monitoring electrodes to conduct electronic monitoring.

40. The system of claim 32, wherein the computer processor is further programmed to input the image data to analyze one or more characteristics of the electronically monitored data.

41. The system of claim 40, wherein the computer processor is further programmed to identify via the image data a mechanism contributing to the one or more characteristics of the electronically monitored data, the mechanism not being readily identifiable by analyzing the electronically monitored data alone.

42. The system of claim 32, wherein the computer processor is further programmed to use the electronically monitored data to analyze one or more characteristics of the image data.

43. The system of claim 42, wherein the computer processor is further programmed to use the electronically monitored data to identify a mechanism contributing to the one or more characteristics of the image data, the mechanism not being readily identifiable by analyzing the acquired image data alone.

44. The system of claim 32, wherein the optical imaging module further comprises an excitation light source configured to excite one or more molecules in the biological samples.

45. The system of claim 44, wherein the excitation light source comprises one or more lights selected from the group consisting of an ultraviolet light, a violet light, a blue light, a green light, a yellow light, an orange light, and a red light.

46. The system of claim 34, The system of claim 1, wherein the wells are sequentially imaged via motion of the optical imaging module.

47. The system of claim 32, wherein electrically monitoring the plurality of biological samples is performed over a period of time to report impedance values directly, without input from a human user, and wherein capturing the image data of the one or more of the plurality of biological samples across the plurality of wells is performed within the period of time.

* * * * *

UNITED STATES PATENT AND TRADEMARK OFFICE
CERTIFICATE OF CORRECTION

PATENT NO. : 12,049,615 B2
APPLICATION NO. : 18/194277
DATED : July 30, 2024
INVENTOR(S) : Nan Li et al.

Page 1 of 1

It is certified that error appears in the above-identified patent and that said Letters Patent is hereby corrected as shown below:

In the Claims

At Column 32, Claim number 46, Line number 40, delete "The system of claim 34, The system of claim 1," and insert -- The system of claim 32, --.

Signed and Sealed this
Nineteenth Day of November, 2024

Katherine Kelly Vidal
*Director of the United States Patent and Trademark Office*